United States Patent
Veyrier et al.

(10) Patent No.: US 12,421,264 B2
(45) Date of Patent: Sep. 23, 2025

(54) **COMPOUNDS AND METHODS FOR THE TREATMENT OF PATHOGENIC *NEISSERIA***

(71) Applicant: INSTITUT NATIONAL DE LA RECHERCHE SCIENTIFIQUE, Québec (CA)

(72) Inventors: Frédéric Veyrier, Montréal (CA); Annie Castonguay, Montréal (CA)

(73) Assignee: INSTITUT NATIONAL DE LA RECHERCHE SCIENTIFIQUE, Québec (CA)

(*) Notice: Subject to any disclaimer, the term of this patent is extended or adjusted under 35 U.S.C. 154(b) by 818 days.

(21) Appl. No.: 17/250,847

(22) PCT Filed: Sep. 11, 2019

(86) PCT No.: PCT/CA2019/051284
§ 371 (c)(1),
(2) Date: Mar. 11, 2021

(87) PCT Pub. No.: WO2020/051701
PCT Pub. Date: Mar. 19, 2020

(65) Prior Publication Data
US 2022/0089626 A1    Mar. 24, 2022

Related U.S. Application Data

(60) Provisional application No. 62/730,062, filed on Sep. 12, 2018.

(51) Int. Cl.
C07F 17/02    (2006.01)
C07F 5/02    (2006.01)

(52) U.S. Cl.
CPC ............... *C07F 17/02* (2013.01); *C07F 5/02* (2013.01)

(58) Field of Classification Search
None
See application file for complete search history.

(56) References Cited

U.S. PATENT DOCUMENTS 3,227,172 A * 1/1966 Sims ..................... B21B 37/50
                                                           251/337
3,277,172 A * 10/1966 Alicino .................. C07F 5/027
                                                            552/205

(Continued)

FOREIGN PATENT DOCUMENTS

WO    WO/0075142 A2    12/2000

OTHER PUBLICATIONS

Hook EW 3rd, Kirkcaldy RD. A Brief History of Evolving Diagnostics and Therapy for Gonorrhea: Lessons Learned. Clin Infect Dis. Sep. 28, 2018;67(8):1294-1299. doi: 10.1093/cid/ciy271. PMID: 29659749; PMCID: PMC6452490. (Year: 2018).*

(Continued)

*Primary Examiner* — Jeffrey S Lundgren
*Assistant Examiner* — Anthony Joseph Seitz
(74) *Attorney, Agent, or Firm* — Lavery, de Billy, L.L.P.; Isabelle Pelletier

(57) ABSTRACT

Tetracoordinate organoborate compounds, such as compounds harboring a tetraarylborate anion or a triarylalkylborate anion, are shown to exhibit a selective bacteriostatic and bactericidal effect against pathogenic *Neisseria* species such as *N. meningitidis* N and *N. gonorrhoeae*. Exemplified active compounds include the tetraphenylborate anion (BPh$_4$-) and a cyclic zwitterionic borinic acid ethanolamine ester. The use of such borate compounds for the treatment of pathogenic *Neisseria* infections is also described.

20 Claims, 10 Drawing Sheets

(56) References Cited

U.S. PATENT DOCUMENTS

| | | | |
|---|---|---|---|
| 2004/0259833 A1* | 12/2004 | Benkovic | C07H 19/20 514/263.2 |
| 2005/0054644 A1 | 3/2005 | Lee et al. | |
| 2005/0227933 A1 | 10/2005 | Benkovic et al. | |

OTHER PUBLICATIONS

Tapsall JW. Antibiotic resistance in Neisseria gonorrhoeae. Clin Infect Dis. Aug. 15, 2005;41 Suppl 4:S263-8. doi: 10.1086/430787. PMID: 16032562. (Year: 2005).*

Walker et al., Journal of Organometallic Chemistry, vol. 761, 2014, pp. 56-63 (Year: 2014).*

Updegraff, The Journal of Infectious Diseases, vol. 114, No. 4 (Oct. 1964), pp. 304-310 (Year: 1964).*

Cess M. Verduin et al., Moraxella catarrhalis: from Emerging to Established Pathogen, Clin. Microbiol, Rev., 2002, vol. 15, No. 1, pp. 125-144.

Neisseria, NCBI Taxonomy ID 482, National Library of Medicine, National Center for Biotechnology Information, (2024).

Moraxella, NCBI Taxonomy ID 475, National Library of Medicine, National Center for Biotechnology Information, (2024).

Sene et al., Coordination Networks Based on Boronate and Benzoxaborolate Ligands. Crystals, MDPI, 2016, Crystals, 6 (5), pp. 48. 10.3390/cryst6050048. hal-01313402.

Jones et al., Antimicrobial activity of LBM415 (NVP PDF-713) tested against pathogenic *Neisseria* spp. (*Neisseria gonorrhoeae* and *Neisseria meningitidis*), Diagnostic Microbiology and Infectious Disease 51 (2005) 139-141.

Chemical Abstracts Service (CAS) Registry Nos. 143-66-8; 18114-68-8; 78885-82-2; 1003 20-28-3; 591751-70-1; 65859-86-1; 1610797-99-3; 1161879-26-0; 1988698-94-7; 1988699-26-8; 53113-48-7; 15738-23-5; 25776-12-9; 1610526-01-6; 1610526-00-5; 15614-89-8, (2021).

Golbaghi et al., Organoruthenium(II) Complexes Bearing an Aromatase Inhibitor: Synthesis, Characterization, in Vitro Biological Activity and in Vivo Toxicity in Zebrafish Embryos, Organametallics 2019, 38, 702-711.

Haghdoost et al., Synthesis, characterization and biological evaluation of cationic organoruthenium(11) fluorene complexes: influence of the nature of the counteranion. Dalton Trans. 2019. 48. 13396-13405.

Liu et al., Non-pathogenic Neisseria: members of an abundant, multi-habitat, diverse genus. Microbiology (2015), 161, 1297-1312.

International Search Report and Written Opinion in respect of PCT/CA2019/051284, (2019).

Shawar et al., Rapid Screening of Natural Products for Antimycobacterial Activity by Using Luciferase-Expressing Strains of *Mycobacterium bovis* BCG and *Mycobacterium intracellulare*. Antimicrob Agents Chemother. Mar. 1997; 41(3): 570-574.

Veyrier et al., A Novel Metal Transporter Mediating Manganese Export (MntX) Regulates the Mn to Fe Intracellular Ratio and Neisseria meningitidis Virulence. PLoS Pathogens. 2011. vol. 7(9): e1002261.

Guiddir et al., Lipocalin 2 in cerebrospinal fluid as a marker of acute bacterial meningitis. BMC Infectious Diseases 2014, 14:276.

Bennett et al. Independent evolution of the core and accessory gene sets in the genus *Neisseria*: insights gained from the genome of Neisseria lactamica isolate 020-06. BMC Genomics 2010, 11:652.

El-Dine et al., Expanding the Balz-Schiemann Reaction: Organotrifluoroborates Serve as Competent Sources of Fluoride Ion for Fluoro-Dediazoniation. Chem. Eur. J. 2018, 24, 14933-14937.

Roman et al., Rapid determination of octanol-water partition coefficient usingvortex-assisted liquid-liquid microextraction. Journal of Chromatography A, 1330 (2014) 1-5.

Walker et al., The synthesis of an anionic, tetraphenylborate-functionalized, [P,N]-hybrid phosphinobenzimidazole ligand and its hemilabile behaviour in ruthenium zwitterion chemistry. Journal of Organometallic Chemistry 761 (2014) 56-63.

Yiantzi et al. Vortex-assisted liquid-liquid microextraction of octylphenol, nonylphenol and bisphenol-A. Talanta 80 (2010) 2057-2062.

Wang et al., Frustrated Lewis Pair Polymers as Responsive Self-Healing Gels. J. Am. Chem. Soc. 2017, 139, 14232-14236.

Ito et al. Palladium-Catalyzed Cross-Coupling Reaction of Potassium Diaryldifluoroborates with Aryl Halides. Synlett 2003, No. 10, 1435-1438.

\* cited by examiner

| Compounds | RLU (+/- SD) |
|---|---|
| DMSO | 65618 (+/- 5347) |
| Erythromycin (4uM) | 503 (+/-107) |
| B02 (MAGA0015) | 212 (+/- 14) |
| AnI-3 | 275 (+/-29) |
| AnII-3 | 524 (+/- 13) |
| AnII-4 | 515 (+/- 69) |
| AnII-6 | 479 (+/- 59) |
| AnII-10 | 528 (+/- 42) |
| AnII-12 | 253 (+/- 64) |
| AnII-13 | 341 (+/- 92) |
| AnII-14 | 418 (+/- 202) |
| AnII-16 | 586 (+/- 203) |
| AnII-18 | 658 (+/- 45) |
| AnII-20 | 484 (+/-27) |
| AnII-21 | 319 (+/- 19) |
| AnII-22 | 512 (+/- 162) |
| AnIII-6 | 359 (+/-82) |
| AnIII-7 | 208 (+/-46) |
| AnIII-8 | 117 (+/-34) |

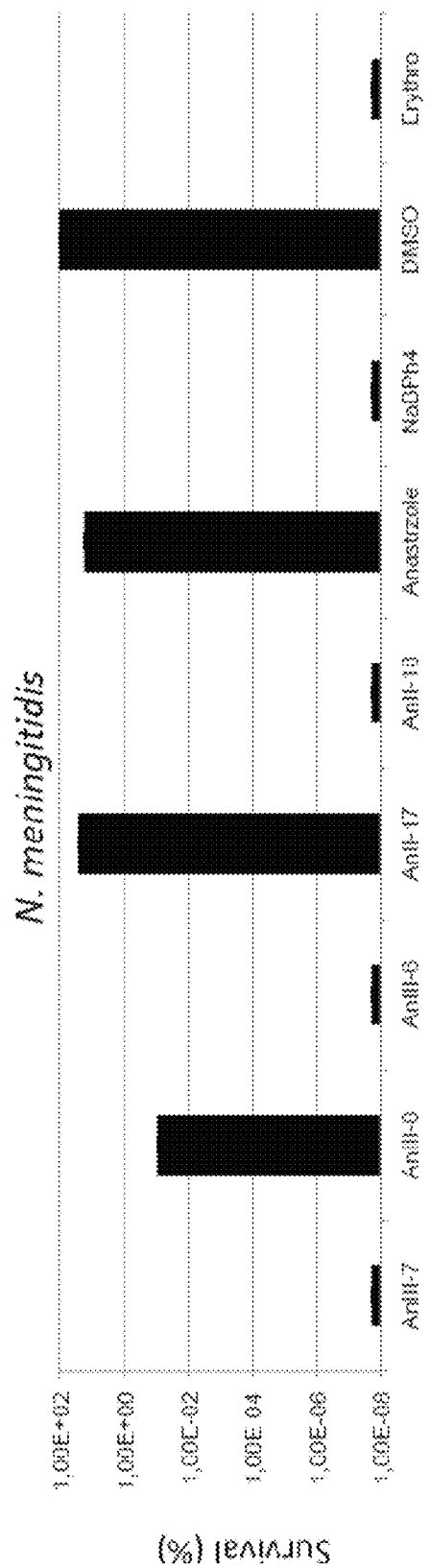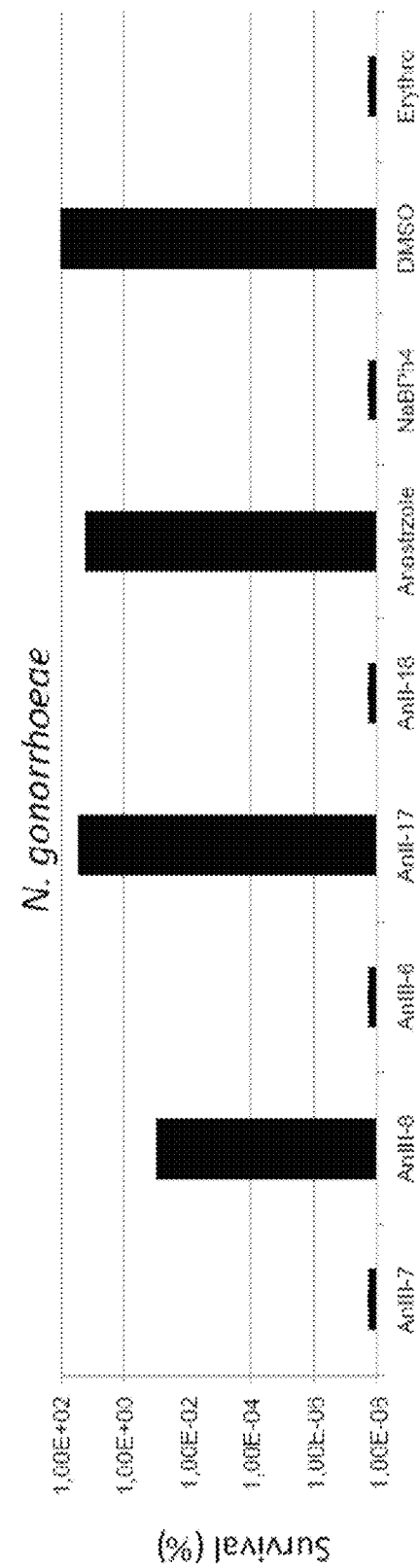
FIG. 2A
FIG. 2B

AnIII-7

AnIII-8

AnIII-6

NaBPh4

AnII-17

AnII-18

COMPOUNDS AND METHODS FOR THE TREATMENT OF PATHOGENIC *NEISSERIA*

CROSS-REFERENCE TO RELATED APPLICATIONS

This application is a National Entry Application of PCT application no PCT/CA2019/051284 filed on Sep. 11, 2019 and published in English under PCT Article 21 (2), which itself claims benefit of U.S. provisional application Ser. No. 62/730,062 filed on Sep. 12, 2018. All documents above are incorporated herein in their entirety by reference.

TECHNICAL FIELD

The present invention generally relates to bacterial infections, and more specifically to the treatment of pathogenic *Neisseria* infections.

BACKGROUND ART

*Neisseria* is a large genus of Gram-negative bacteria that colonize the mucosal surfaces of many animals, including humans. Of the species that colonize humans, only two are pathogens, *N. meningitidis* and *N. gonorrhoeae*. *Neisseria meningitidis* and *Neisseria gonorrhoeae* constitute major human treats. *N. meningitidis* causes life-threatening diseases such as meningitis and sepsis (0.15 million deaths/year) whereas *N. gonorrhoeae* is the causative agent of gonorrhea (also called the clap), a sexually transmitted disease (88 million cases/year). Both species are highly related, as they have emerged from a common commensal symbiont ancestor. Vaccine and antibiotics are currently minimally preventing a devastating global epidemic but unfortunately some strains are rapidly evolving to escape those two types of human interventions. Notably, *N. gonorrhoeae* currently generates drug resistance (particularly ceftriaxone resistance) with a high risk of untreatable infection emergence. Furthermore, most antibiotic treatments are not selective for pathogenic *Neisseria*, and thus affect the normal human microbiome. As a result, it is now urgent to develop new avenues of treatments to fight these bacteria (WHO).

Non-pathogenic *Neisseria* species constitute a significant component of the normal human microbiome, and notably colonize the human oral and nasopharyngeal cavities as well as the genito-urinary tract (Liu et al., Microbiology (2015), 161, 1297-1312). As this commensal population of bacteria may contribute to human health, any treatment against infections by the pathogenic *Neisseria* species (*Neisseria meningitidis* and *Neisseria gonorrhoeae*) should ideally have as little effect as possible against the non-pathogenic *Neisseria* species.

The present description refers to a number of documents, the content of which is herein incorporated by reference in their entirety.

SUMMARY OF THE INVENTION

The present disclosure provides the following items:
1. A borate compound of formula (I):

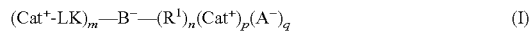

$$(Cat^+\text{-}LK)_m\text{—}B^-\text{—}(R^1)_n(Cat^+)_p(A^-)_q \quad (I)$$

wherein:
  m and n are integers from 0 to 4, with the proviso that m+n=4,
  p is an integer and is the larger of 0 and 1-m,
  q is an integer and is the larger of 0 and m-1,
  each $R^1$ independently represents:
    alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being unsubstituted or substituted with one or more of the following: —$R^2$, —$OR^2$, —$P(R^2)_2$, —$SR_2$, —O—CO—$R^2$, —CO—O—$R^2$, —CO—$R^2$, —CO—N$(R^2)_2$, —N$(R^2)_2$, —N$R_2$—CO—$R^2$, —C=N$R_2$, —C≡N, —NO$_2$, —N$_3$, halogen, or -LK-$R^3$, or
    —H, —$OR^2$, —$P(R^2)_2$, —$SR_2$, —O—CO—$R^2$, —CO—O—$R^2$, —CO—$R^2$, —CO—N$(R^2)_2$, —N$(R^2)_2$, —N$R_2$—CO—$R^2$, —C=N$R_2$, —C≡N, —NO$_2$, —N$_3$, halogen, or -LK-$R^3$, and/or
  two $R^1$ together with the boron atom to which they are attached form a cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being unsubstituted or substituted with one or more of the following: —$R^2$, —$OR^2$, —$P(R^2)_2$, —$SR_2$, —O—CO—$R^2$, —CO—O—$R^2$, —CO—$R^2$, —CO—N$(R^2)_2$, —N$(R^2)_2$, —N$R_2$—CO—$R^2$, —C=N$R_2$, —C≡N, —NO$_2$, —N$_3$, halogen, or -LK-$R^3$,
  each $R^2$ independently represents:
    alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being unsubstituted or substituted with one or more of the following: —$R^4$, —$OR^4$, —$P(R^4)_2$, —$SR_4$, —O—CO—$R^4$, —CO—O—$R^4$, —CO—$R^4$, —CO—N$(R^4)_2$, —N$(R^4)_2$, —N$R_4$—CO—$R^4$, —C=N$R_4$, —C≡N, —NO$_2$, —N$_3$, halogen, or -LK-$R^3$, or
    H, —OH, —$P(R^4)_2$, —SH, —O—CO—H, —COOH, —CO—H, —CO—NH$_2$, —NH$_2$, —NH—CO—H, —C=NH, —C≡N, —NO$_2$, —N$_3$, halogen, or -LK-$R^3$,
  each $R^3$ independently represents is a pharmaceutically acceptable compound; each $R^4$ independently represents: H, alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, heteroaryl, —OH, —SH, —O—CO—H, —COOH, —CO—H, —CO—NH$_2$, —NH$_2$, —NH—CO—H, —C=NH, —C≡N, —NO$_2$, —N$_3$, halogen, or -LK-$R^3$,
  each -LK- independently represents a covalent bond or a linking group,
  each $Cat^+$ independently represents a pharmaceutically acceptable cation, and
  each $A^-$ independently represents a pharmaceutically acceptable anion,
  with the proviso that no more than two $R^1$ are halogen.
2. The borate compound of item 1, wherein m is 0 or 1.
3. The borate compound of item 2, wherein m is 0.
4. The borate compound of item 2, wherein m is 1.

5. The borate compound of any one of items 1 to 4, wherein no more than one $R^1$ is halogen, and preferably no $R^1$ is halogen.

6. The borate compound of any one of items 1 to 5, wherein each $R^1$ is independently alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being:
   unsubstituted or substituted with one or more (preferably one) —$R^2$, —$OR^2$, —$P(R^2)_2$, —$SR^2$, —O—CO—$R^2$, —CO—O—$R^2$, —CO—$R^2$, —CO—N($R^2)_2$, —N($R^2)_2$, —$NR^2$—CO—$R^2$, —C=$NR^2$, —C≡N, —$NO_2$, —$N_3$, halogen, or -LK-$R^3$,
   more preferably unsubstituted or substituted with one or more (preferably one) —$R^2$, —N($R^2)_2$, or -LK-$R^3$;
   yet more preferably either of:
      unsubstituted,
      substituted with one —$R^2$,
      substituted with one —N($R^2)_2$, or
      substituted with one -LK-$R^3$.

7. The borate compound of item 6, wherein each $R^1$ is independently aryl or heteroaryl, preferably aryl, more preferably phenyl, all of which being:
   unsubstituted or substituted with one or more (preferably one) —$R^2$, —$OR^2$, —$P(R^2)_2$, —$SR^2$, —O—CO—$R^2$, —CO—O—$R^2$, —CO—$R^2$, —CO—N($R^2)_2$, —N($R^2)_2$, —$NR^2$—CO—$R^2$, —C=$NR^2$, —C≡N, —$NO_2$, —$N_3$, halogen, or -LK-$R^3$;
   preferably unsubstituted or substituted with one or more (preferably one) —$R^2$ or -LK-$R^3$,
   more preferably unsubstituted or substituted with one -LK-$R^3$;
   yet more preferably either of:
      unsubstituted,
      substituted with one —$R^2$
      substituted with one —N($R^2)_2$, or
      substituted with one -LK-$R^3$.

8. The borate compound of item 6, wherein:
   one or more, preferably one, $R^1$ group is alkyl, alkenyl, alkynyl, or alkenynyl, preferably alkyl, and more preferably $C_5$-$C_{12}$ alkyl, all of which being unsubstituted or substituted as described in item 1, preferably unsubstituted, and
   the remaining $R^1$ groups are aryl or heteroaryl, preferably aryl, more preferably phenyl, all of which being unsubstituted or substituted as described in item 1, preferably unsubstituted.

The borate compound of item 6, wherein each $R^1$ is independently aryl or heteroaryl, preferably aryl, more preferably phenyl, wherein:
   one, two, three, or all of the aryl and/or heteroaryl are substituted as described in item 1, preferably substituted with one or more —$R^2$, and more preferably substituted with one —$R^2$, and
   the remaining aryl and/or heteroaryl are unsubstituted.

9. The borate compound of item 9, wherein two, three or all of the aryl and/or heteroaryl are substituted with one or more (preferably one) —$R^2$, and
   preferably three or all of the aryl and/or heteroaryl are substituted with one or more (preferably one) —$R^2$, and
   yet more preferably all of the aryl and/or heteroaryl are substituted with one or more (preferably one) —$R^2$.

10. The borate compound of item 9, wherein one of the aryl and/or heteroaryl are substituted with one or more (preferably one) —$R^2$.

11. The borate compound of any one of items 1 to 5, wherein:
    one or two $R^1$ are halogen, preferably F, and
    the remaining $R^1$ are aryl or heteroaryl, preferably aryl, more preferably phenyl, all of which being unsubstituted or substituted as described in item 1, preferably unsubstituted.

12. The borate compound of any one of items 1 to 5, wherein:
    two $R^1$ together with the boron atom to which they are attached form a:
       cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, preferably heterocycloalkyl,
       more preferably 1,3,2-oxazaborolidin-3-ium-2-uidyl (i.e.

wherein the dot represent the point of attachment of the two other groups (i.e. the Cat⁺-LK- and/or the remaining $R^1$) on the boron atom), all of which being:
       unsubstituted or substituted with one or more of the following: —$R^2$, —$OR^2$, —$P(R^2)_2$, —$SR^2$, —O—CO—$R^2$, —CO—O—$R^2$, —CO—$R^2$, —CO—N($R^2)_2$, —N($R^2)_2$, —$NR^2$—CO—$R^2$, —C=$NR^2$, —C≡N,2019-09-06 —$NO_2$, —$N_3$, halogen, or -LK-$R^3$, preferably unsubstituted, and
    each of the remaining $R^1$ is independently:
       alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl,
       preferably aryl or heteroaryl, more preferably aryl, yet more preferably phenyl all of which being:
          unsubstituted or substituted with one or more of the following: —$R^2$, —$OR^2$, —$P(R^2)_2$, —$SR^2$, —O—CO—$R^2$, —CO—O—$R^2$, —CO—$R^2$, —CO—N($R^2)_2$, —N($R^2)_2$, —$NR^2$—CO—$R^2$, —C=$NR^2$, —C≡N, —$NO_2$, —$N_3$, halogen, or -LK-$R^3$, preferably unsubstituted.

13. The borate compound of any one of items 1 to 13 (preferably items 9 to 11, more preferably item 10), wherein $R^2$ is:
    alkyl (preferably C1-$C_6$ alkyl, more preferably methyl), alkenyl, alkynyl, alkenynyl, a halogen atom (preferably F or 1), or —C≡N;
    preferably alkyl (preferably C1-$C_6$ alkyl, more preferably methyl), halogen (preferably F or 1), or —C≡N;
    more preferably halogen (preferably F or 1).

14. The borate compound of any one of items 1 to 13 (preferably items 9 to 11, more preferably item 11), wherein $R^2$ is aryl or heteroaryl, preferably heteroaryl, preferably benzimidazol-1-yl, more preferably benzimidazol-1-yl, all of which being:

unsubstituted or substituted with one or more of the following: —R⁴, —OR⁴, —P(R⁴)₂, —SR⁴, —O—CO—R⁴, —CO—O—R⁴, —CO—R⁴, —CO—N(R⁴)₂, —N(R⁴)₂, —NR⁴—CO—R⁴, —C=NR⁴, —C≡N, —NO₂, —N₃, halogen, or -LK-R³, preferably unsubstituted or substituted with one of the following: —R⁴, —OR⁴, —P(R⁴)₂, —SR⁴, —O—CO—R⁴, —CO—O—R⁴, —CO—R⁴, —CO—N(R⁴)₂, —N(R⁴)₂, —NR⁴—CO—R⁴, —C=NR⁴, —C≡N, —NO₂, —N₃, halogen, or -LK-R³, more preferably substituted with one of the following: —R⁴, —OR⁴, —P(R⁴)₂, —SR⁴, —O—CO—R⁴, —CO—O—R⁴, —CO—R⁴, —CO—N(R⁴)₂, —N(R⁴)₂, —NR⁴—CO—R⁴, —C=NR⁴, —C≡N, —NO₂, —N₃, halogen, or -LK-R³, yet more preferably substituted with one —P(R⁴)₂.

15. The borate compound of any one of items 1 to 15, wherein (preferably when R² is part of a —N(R²)₂ group), R² is:
—H, aryl or heteroaryl,
preferably one R² is —H and the other R² is aryl or heteroaryl,
wherein the aryl or heteroaryl is preferably aryl, more preferably naphthyl, and
wherein the aryl and heteroaryl are:
unsubstituted or substituted with one or more of the following: —R⁴, —OR⁴, —P(R⁴)₂, —SR⁴, —O—CO—R⁴, —CO—O—R⁴, —CO—R⁴, —CO—N(R⁴)₂, —N(R⁴)₂, —NR⁴—CO—R⁴, —C=NR⁴, —C≡N, —NO₂, —N₃, halogen, or -LK-R³,
preferably unsubstituted or substituted with one of the following: —R⁴, —OR⁴, —P(R⁴)₂, —SR⁴, —O—CO—R⁴, —CO—O—R⁴, —CO—R⁴, —CO—N(R⁴)₂, —N(R⁴)₂, —NR⁴—CO—R⁴, —C=NR⁴, —C≡N, —NO₂, —N₃, halogen, or -LK-R³,
more preferably substituted with one of the following: —R⁴, —OR⁴, —P(R⁴)₂, —SR⁴, —O—CO—R⁴, —CO—O—R⁴, —CO—R⁴, —CO—N(R⁴)₂, —N(R⁴)₂, —NR⁴—CO—R⁴, —C=NR⁴, —C≡N, —NO₂, —N₃, halogen, or -LK-R³,
yet more preferably substituted with one —OR⁴.

16. The borate compound of any one of items 1 to 16, wherein (preferably when R⁴ is part of a —OR⁴ group), R⁴ is H.

17. The borate compound of any one of items 1 to 16, wherein (preferably when R⁴ is part of a —P(R⁴)₂ group), R⁴ is aryl or heteroaryl, preferably aryl, more preferably phenyl.

18. The borate compound of any one of items 1 to 18, wherein -LK- represents a covalent bond or one or more of the following, alone or in combination, amide, amine, imine, —C(=O)—, —S—, —S—S—, —O—, ester, alkylene, alkenylene, alkynylene, alkenylnylene, cycloalkylene, cycloalkenylene, cycloalkynylene, cycloalkenynylene, heterocycloalkylene, heterocycloalkenylene, heterocycloalkynylene, heterocycloalkenynylene, arylene, or heteroarylene.

19. The borate compound of item 19, wherein -LK- represents a covalent bond or one or more of the following, alone or in combination, —O—, alkylene, alkenylene, alkynylene, alkenylnylene, or heteroarylene.

20. The borate compound of item 19 or 20, wherein -LK- represents alkylene combined with —O— to form one or more alkyleneoxy groups, preferably one or more ethyleneoxy groups.

21. The borate compound of item 19 or 20, wherein -LK- represents heteroarylene, preferably triazolylene, more preferably 1,2,3-triazolylene, and yet more preferably 1,2,3-triazol-1,4-ylene, alone or combined with one or more of the following groups, preferably two of the following groups, and more preferably one of the following groups on each side of the heteroarylene: alkylene, alkenylene, alkynylene, or alkenylnylene, preferably alkylene, and more preferably methylene.

22. The borate compound of item 22, wherein -LK- represents

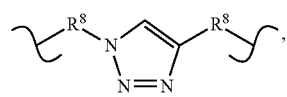

wherein each R8 is independently alkylene, alkenylene, alkynylene, or alkenylnylene, preferably alkylene, and more preferably methylene.

23. The borate compound of item 19 or 20, wherein -LK- represents arylene, preferably phenylene, more preferably paraphenylene, alone or combined with one or more (preferably one) of the following groups: alkylene, alkenylene, alkynylene, or alkenylnylene groups, preferably alkylene, and more preferably methylene.

24. The borate compound of item 24, wherein -LK- represents

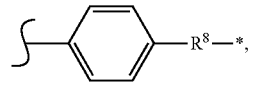

wherein R⁸ is independently alkylene, alkenylene, alkynylene, or alkenylnylene, preferably alkylene, more preferably methylene.

25. The borate compound of item 19 or 20, wherein -LK- represents a covalent bond.

26. The borate compound of any one of items 1 to 26, wherein R³ represents a pharmaceutically acceptable compound that is pharmaceutically inactive.

27. The borate compound of any one of items 1 to 26, wherein R³ represents a pharmaceutically acceptable compound that is pharmaceutically active.

28. The borate compound of item 28, wherein the pharmaceutically active compound is an antibiotic.

29. The borate compound of item 29, wherein the pharmaceutically active compound is an antibiotic conventionally used against *Neisseria* or that has been reported as a promising candidate for use against *Neisseria*.

30. The borate compound of item 28 or 29, wherein the pharmaceutically active compound is a quinolone antibiotic (e.g. ciprofloxacin), a cephalosporin antibiotic (e.g., ceftriaxone, cefixime, cefotaxime), tetracyclin, erythromycin, a penicillin (e.g., penicillin G), chloramphenicol, azithromycin, spectinomycin, doxycycline, gemifloxacin, or gentamicin.

31. The borate compound of any one of items 1 to 28, wherein R³ represents a metal-based complex, preferably a ruthenium complex, and more preferably

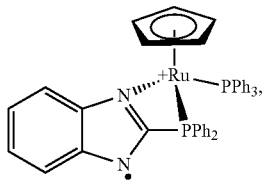

wherein the dot represents the point of attachment.

32. The borate compound of any one of items 1 to 32, wherein the pharmaceutically acceptable cation is:
    an alkali metal cation such as $Na^+$, $Li^+$, and $K^+$;
    an alkaline earth metal cation such as $Ca^{2+}$ and $Mg^{2+}$;
    a metal cation such as aluminum, iron, zinc, copper, nickel and cobalt cations;
    an inorganic amine cation such as ammonium ($NH_4^+$) or substituted ammonium cations such as e.g. ethyl ammonium, diethylammonium, trimethylammonium tetraethylammonium, tetramethylammonium and tetrabutylammonium cations;
    a cation of an organic bases, for example, an organic amines, such as chloroprocaine, dibenzylamine, dicyclohexylamine, dicyclohexylamines, diethanolamine, ethylamine (including diethylamine and triethylamine), ethylenediamine, glucosamine, guanidine, methylamine (including dimethylamine and trimethylamine), morpholine, choline, N,N'-dibenzylethylenediamine, N-benzyl-phenethylamine, N-methylglucamine, phenylglycine alkyl ester, piperazine, piperidine, procaine, t-butyl amines, tetramethylammonium, t-octylamine, tris-(2-hydroxyethyl) amine, and tris(hydroxymethyl)aminomethane cations; or cationic metal-based complexes, such as cationic ruthenium complexes, preferably

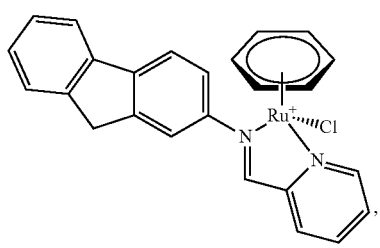

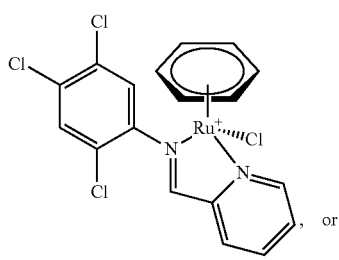

33. The borate compound of item 33, wherein the pharmaceutically acceptable cation is: $Na^+$, $K^+$, $NH_4^+$,

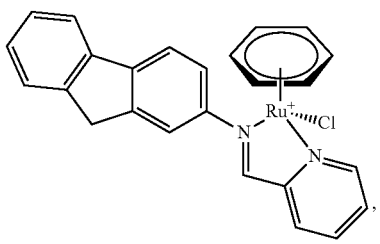

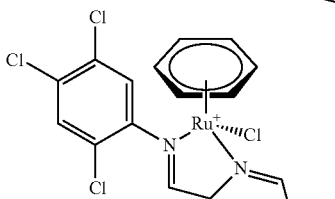

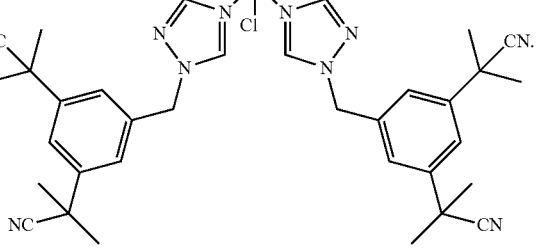

34. The borate compound of any one of items 1 to 34, wherein the pharmaceutically acceptable anion is aceglutamate, acephyllinate, acetamidobenzoate, acetate, acetylasparaginate, acetylaspartate, adipate, aminosalicylate, anhydromethylenecitrate, ascorbate, aspartate, benzoate, benzylate, besylate, bicarbonate, bisulphate, bitartrate, borate, bromide, butylbromide, camphorate, camsylate, carbonate, chloride, chlorophemoxyacetate, citrate, closylate, cromesilate, cyclamate, dehydrochloate, dihydrochloride, dimalonate, edetate, edisylate, estolate, esylate, ethylbromide, ethylsulfate, fendizoate, fluoride, formate, fosfatex, fumarate, gluceptate, gluconate, glucoronate, glutamate, glycerophosphate, glycinate, glycollylarsinilate, glycyrrhizate, hippurate, hemisulphate, hexylresorcinate, hybenzate, hydrobromide, hydrochloride, hydroiodide, hydroxybenzenesulfonate, hydroxybenzoate, iodide, isethionate, lactate, lactobionate, lysine, malate, maleate, mandalate, mesylate, methylbromide, methyliodide, methylnitrate, methylsulphate, monophosadenine, mucate, napadisylate, napsylate, nicotinate, nitrate, oleate, orotate, oxalate, oxoglurate, pamoate, pantothenate, pectinate, phenylethylbarbiturate, phosphate, picrate, policrilix, polistirex, pyridoxylphosphate, polygalacturonate, propionate, saccharinate, salicylate, stearate, stearylsulphate, subacetate, succinate, sulfate, sulfosalicylate, tannate, tartrate, teprosilate, terephthalate, teoclate, thiocyanate, timonaciate, tosylate, triethiodide, undecanoate, and xinafoate. Preferred anions include acetate, besylate, bisulphate, bromide, carbonate, chloride, citrate, fluoride, formate, iodide, maleate, mesylate, methylsulphate, nitrate, nitrite, pamoate, phosphate, stearate, sulfate, or tartrate.

35. The borate compound of any one of items 1 to 35, being of formula:

(IV)
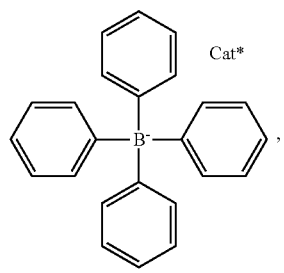

(V)
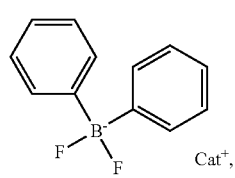

(VI)
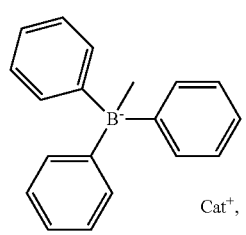

(VII)
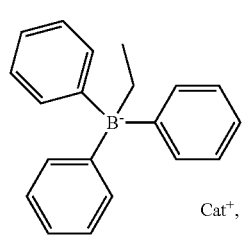

-continued (VIII)
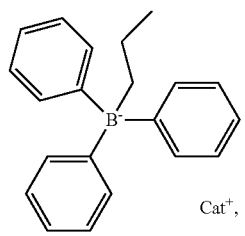

(IX)
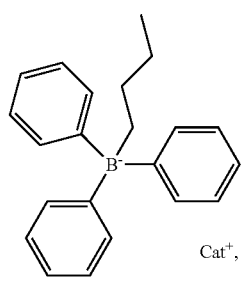

(X)
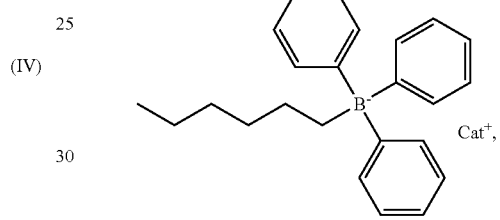

(XI)
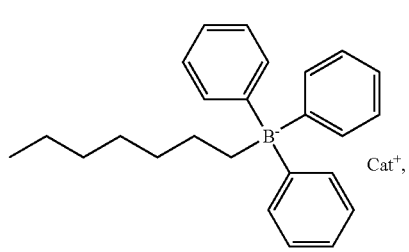

(XII)
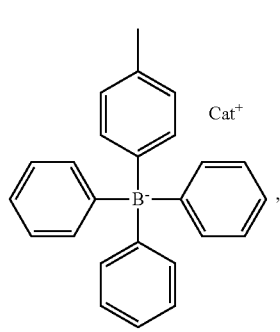

(XIII)
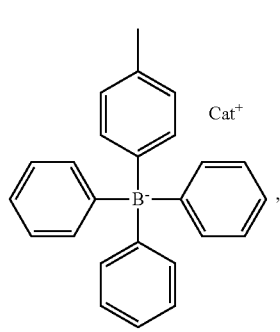

(XIV)
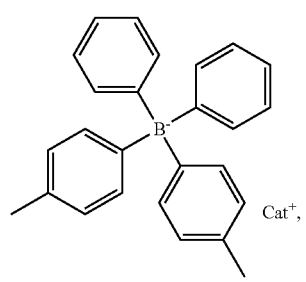
Cat⁺,
(XV)
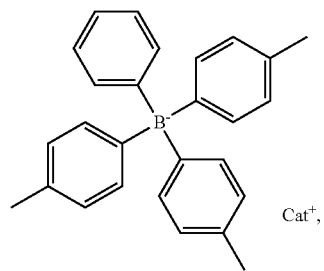
Cat⁺,
(XVI)
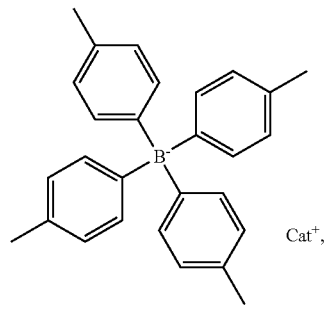
Cat⁺,
(XVII)
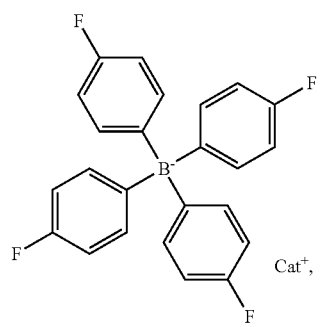
Cat⁺,
(XVIII)
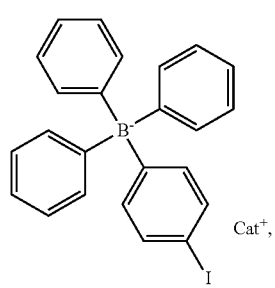
Cat⁺,
(XIX)
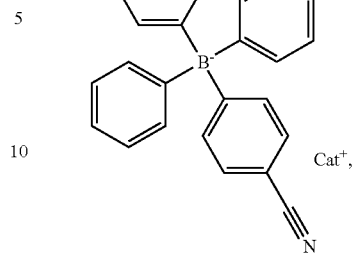
Cat⁺,
(XX)
Cat⁺,
(XXI)
(XXII)
Cat⁺, or
(XXIII)

preferably the borate compound is of formula (IV)-(XXII),
more preferably of formula (VIII)- (XII), (XIV)- (XVIII), or (XX)- (XXII), and
most preferably of formula (X)- (XII), (XXI), or (XXII),
wherein Cat⁺ is as defined in item 1 and is preferably Na⁺, K⁺, NH₄⁺,

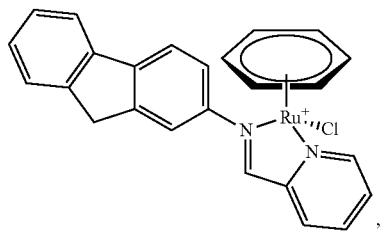

,

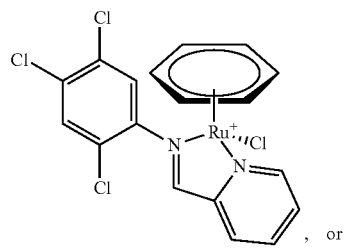

, or

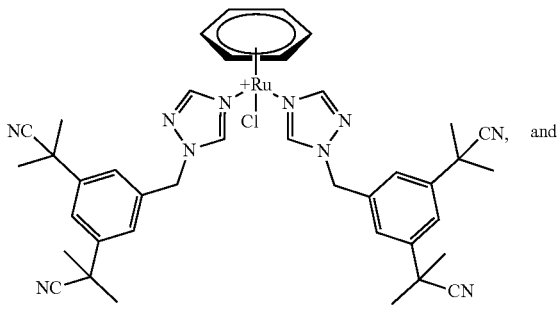

, and more preferably

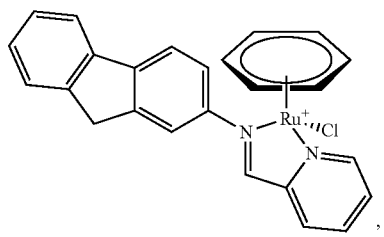

,

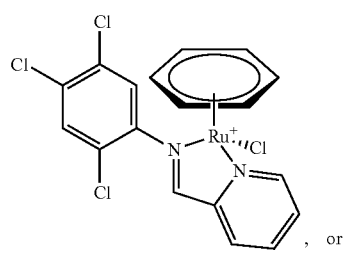

, or

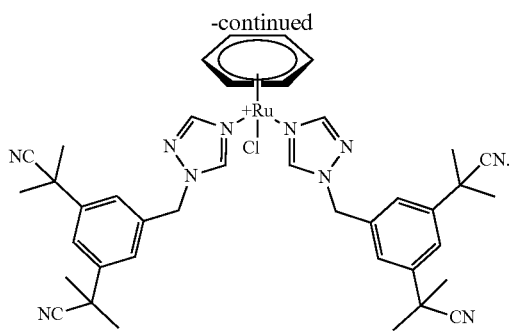

36. The borate compound of any one of items 1 to 36, having a lipophilicity, expressed as log $P_{octanol/water}$, of 0 or more, preferably 0.5 or more, more preferably 1 or more, yet more preferably 1.5 or more, and most preferably 2 of more.
37. A method for treating a pathogenic *Neisseria* infection in a subject comprising administering an effective amount of the borate compound of any one of items 1 to 37 to said subject.
38. A method for inhibiting the growth and/or killing pathogenic *Neisseria* bacteria, the method comprising contacting said pathogenic *Neisseria* bacteria with an effective amount of the borate compound of any one of items 1 to 37.
39. The method of item 38 or 39, wherein the treatment results in the selective growth inhibition and/or killing of the pathogenic *Neisseria* bacteria.
40. The method of any one of items 38-40, wherein the pathogenic *Neisseria* bacteria is *Neisseria meningitidis* and/or *Neisseria gonorrhoeae*.
41. The method of item 41, wherein the pathogenic *Neisseria* bacteria is *Neisseria meningitidis*.
42. The method of item 42, wherein the pathogenic *Neisseria* bacteria is *Neisseria gonorrhoeae*.
43. The method of any one of items 38-43, wherein the pathogenic *Neisseria* bacteria is resistant to one or more antibiotics.
44. The method of any one of items 38-44, wherein the borate compound is formulated into a composition comprising at least one carrier or excipient.
45. The method of item 45, wherein the composition is a pharmaceutical composition.
46. The method of any one of items 38-46, wherein the borate compound is administered or used in combination with at least one additional antibiotic.
47. The method of item 47, wherein the at least one additional antibiotic is a cephalosporin antibiotic, a penicillin antibiotic, chloramphenicol, azithromycin, spectinomycin, doxycycline, gemifloxacin and/or gentamicin.
48. Use of the borate compound of any one of items 1 to 37 for treating a pathogenic *Neisseria* infection in a subject.
49. Use of the borate compound of any one of items 1 to 37 for the manufacture of a medicament for treating a pathogenic *Neisseria* infection in a subject.
50. Use of the borate compound of any one of items 1 to 37 for inhibiting the growth and/or killing pathogenic *Neisseria* bacteria.
51. Use of the borate compound of any one of items 1 to 37 for the manufacture of a medicament for inhibiting the growth and/or killing pathogenic *Neisseria* bacteria.

52. The use of any one of items 49-52, wherein the use results in the selective growth inhibition and/or killing of the pathogenic *Neisseria* bacteria.

53. The use of any one of items 49-52, wherein the pathogenic *Neisseria* bacteria is *Neisseria meningitidis* and/or *Neisseria gonorrhoeae*.

54. The use of item 54, wherein the pathogenic *Neisseria* bacteria is *Neisseria meningitidis*.

55. The use of item 54, wherein the pathogenic *Neisseria* bacteria is *Neisseria gonorrhoeae*.

56. The use of any one of items 49-56, wherein the pathogenic *Neisseria* bacteria is resistant to one or more antibiotics.

57. The use of any one of items 49-57, wherein the borate compound is formulated into a composition comprising at least one carrier or excipient.

58. The use of item 58, wherein the composition is a pharmaceutical composition.

59. The use of any one of items 49-59, wherein the borate compound is used in combination with at least one additional antibiotic.

60. The use of item 60, wherein the at least one additional antibiotic is a cephalosporin antibiotic, a penicillin antibiotic, chloramphenicol, azithromycin, spectinomycin, doxycycline, gemifloxacin and/or gentamicin.

61. The borate compound of any one of items 1 to 37 for treating a pathogenic *Neisseria* infection in a subject.

62. The borate compound of any one of items 1 to 37 for inhibiting the growth and/or killing pathogenic *Neisseria* bacteria.

63. The borate compound for use according to item 62 or 63, wherein the pathogenic *Neisseria* bacteria is *Neisseria meningitidis* and/or *Neisseria gonorrhoeae*.

64. The borate compound for use according to item 64, wherein the pathogenic *Neisseria* bacteria is *Neisseria meningitidis*.

65. The borate compound for use according to item 64, wherein the pathogenic *Neisseria* bacteria is *Neisseria gonorrhoeae*.

66. The borate compound for use according to any one of items 62-66, wherein the pathogenic *Neisseria* bacteria is resistant to one or more antibiotics.

67. The borate compound for use according to any one of items 62-67, wherein the borate compound is formulated into a composition comprising at least one carrier or excipient.

68. The borate compound for use according to item 68, wherein the composition is a pharmaceutical composition.

69. The borate compound for use according to any one of items 62-69, wherein the borate compound is used in combination with at least one additional antibiotic.

70. The borate compound for use according to item 70, wherein the at least one additional antibiotic is a cephalosporin antibiotic, a penicillin antibiotic, chloramphenicol, azithromycin, spectinomycin, doxycycline, gemifloxacin and/or gentamicin.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 2A shows the percentage of survival of *N. meningitidis* following a 3 h treatment with the indicated compounds at a concentration of 50 µM. Each bar represents the average of three independent measurements.

FIG. 2B shows the percentage of survival of *N. gonorrhoeae* following a 3 h treatment with the indicated compounds at a concentration of 50 µM. Each bar represents the average of three independent measurements.

DISCLOSURE OF INVENTION

Figure 1A:
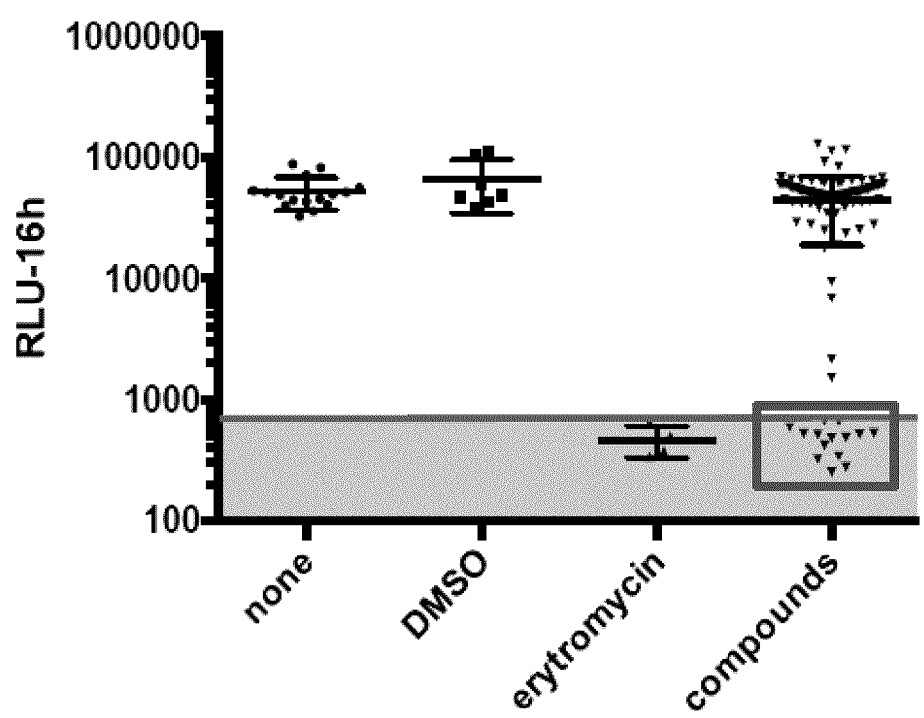
FIG. 1A shows the effect of different compounds tested at 100 µM on the 16 h growth of *N. meningitidis* measured using luciferase-based assay.

In the studies described herein, the present inventors have shown that compounds harboring a tetraphenylborate anion ($BPh_4$) exhibit a selective bacteriostatic and bactericidal effect against pathogenic *Neisseria* species such as *N. meningitidis* and *N. gonorrhoeae*. This anti-pathogenic *Neisseria* activity was obtained with different $BPh_4^-$ salts and compounds harboring a $BPh_4^-$ counterion, but was not shared by another tetrahedral boron ion ($BF_4^-$).

Accordingly, in an aspect, the present disclosure provides a method for treating a pathogenic *Neisseria* infection in a subject comprising administering an effective amount of a borate compound to said subject. In another aspect, the present disclosure provides the use of a borate compound for treating a pathogenic *Neisseria* infection in a subject. In another aspect, the present disclosure provides the use of a borate compound for the manufacture of a medicament for treating a pathogenic *Neisseria* infection in a subject. In another aspect, the present disclosure provides a borate compound for treating a pathogenic *Neisseria* infection in a subject.

In another aspect, the present disclosure provides a method for inhibiting the growth and/or killing pathogenic *Neisseria* bacteria, the method comprising contacting said pathogenic *Neisseria* bacteria with an effective amount of a borate compound. In another aspect, the present disclosure provides the use of a borate compound for inhibiting the growth and/or killing pathogenic *Neisseria* bacteria. In another aspect, the present disclosure provides the use of a borate compound for the manufacture of a medicament for inhibiting the growth and/or killing pathogenic *Neisseria* bacteria. In another aspect, the present disclosure provides a borate compound for inhibiting the growth and/or killing pathogenic *Neisseria* bacteria.

In an embodiment, the borate compound is of formula (I):

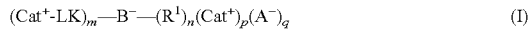

(I)

wherein:
m and n are integers from 0 to 4, with the proviso that m+n=4,
p is an integer and is the larger of 0 and 1-m,
q is an integer and is the larger of 0 and m−1,
  each $R^1$ independently represents:
    alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being unsubstituted or substituted with one or more of the following:—$R^2$, —$OR^2$, —$P(R^2)_2$, —$SR_2$, —$O$—$CO$—$R^2$, —$CO$—$O$—$R^2$, —$CO$—$R^2$, —$CO$—$N(R^2)_2$, —$N(R^2)_2$, —$NR_2$—$CO$—$R^2$, —$C$=$NR_2$, —$C$≡$N$, —$NO_2$, —$N_3$, halogen, or -LK-$R^3$, or
    —H, —$OR^2$, —$P(R^2)_2$, —$SR_2$, —$O$—$CO$—$R^2$, —$CO$—$O$—$R^2$, —$CO$—$R^2$, —$CO$—$N(R^2)_2$, —$N(R^2)_2$, —$NR_2$—$CO$—$R^2$, —$C$=$NR_2$, —$C$≡$N$, —$NO_2$, —$N_3$, halogen, or -LK-$R^3$,
  and/or
  two $R^1$ together with the boron atom to which they are attached form a cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being unsubstituted or substituted with one or more of the following:—$R^2$, —$OR^2$, —$P(R^2)_2$, —$SR_2$, —$O$—$CO$—$R^2$, —$CO$—$O$—$R^2$, —$CO$—$R^2$, —$CO$—$N(R^2)_2$, —$N(R^2)_2$, —$NR_2$—$CO$—$R^2$, —$C$=$NR_2$, —$C$≡$N$, —$NO_2$, —$N_3$, halogen, or -LK-$R^3$,
  each $R^2$ independently represents:
    alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being unsubstituted or substituted with one or more of the following:—$R^4$, —$OR^4$, —$P(R^4)_2$, —$SR_4$, —$O$—$CO$—$R^4$, —$CO$—$O$—$R^4$, —$CO$—$R^4$, —$CO$—$N(R^4)_2$, —$N(R^4)_2$, —$NR_4$—$CO$—$R^4$, —$C$=$NR_4$, —$C$≡$N$, —$NO_2$, —$N_3$, halogen, or -LK-$R^3$, or
    —H, —OH, —$P(R^4)_2$, —SH, —$O$—$CO$—H, —COOH, —$CO$—H, —$CO$—$NH_2$, —$NH_2$, —NH—CO—H, —C=NH, —C≡N, —$NO_2$, —$N_3$, halogen, or -LK-$R^3$, each $R^3$ independently represents is a pharmaceutically acceptable compound;
  each $R^4$ independently represents: H, alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, heteroaryl, —OH, —SH, —O—CO—H, —COOH, —CO—H, —CO—NH2, —NH2, —NH—CO—H, —C=NH, —C≡N, —$NO_2$, —$N_3$, halogen, or -LK-$R^3$,
  each -LK- independently represents a covalent bond or a linking group,
  each $Cat^+$ independently represents a pharmaceutically acceptable cation, and
  each $A^−$ independently represents a pharmaceutically acceptable anion, with the proviso that no more than two $R^1$ are halogen.

In preferred embodiments, m is 0 or 1. In more preferred embodiments, m is 0. In alternative more preferred embodiments, m is 1. When m is 0, the borate compound is of formula (II) below. When m is 1, the borate compound is of formula (III).

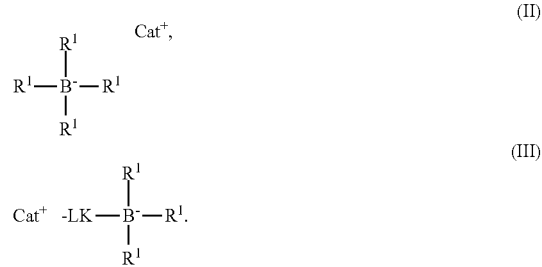

It will be apparent to a skilled person that, although the $Cat^+$-LK- and $R^1$ groups are represented in a single plane in Formulas (I) to (III) above; in fact, it is well-known that these groups arrange themselves as a tetrahedron.

In preferred embodiments, no more than one $R^1$ is halogen. In more preferred embodiments, no $R^1$ is halogen.

In alternative embodiments in which one or more $R^1$ is halogen, the halogen is preferably F.

In preferred embodiments, each $R^1$ is independently alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being:
  unsubstituted or substituted with one or more (preferably one) —$R^2$, —$OR^2$, —$P(R^2)_2$, —$SR^2$, —$O$—$CO$—$R^2$, —$CO$—$O$—$R^2$, —$CO$—$R^2$, —$CO$—$N(R^2)_2$, —$N(R^2)_2$, —$NR^2$—$CO$—$R^2$, —$C$=$NR^2$, —$C$≡$N$, —$NO_2$, —$N_3$, halogen, or -LK-$R^3$,
  more preferably unsubstituted or substituted with one or more (preferably one) —$R^2$, —$N(R^2)_2$, or -LK-$R^3$;
  yet more preferably either of:
    unsubstituted,
    substituted with one —$R^2$
    substituted with one —$N(R^2)_2$, or
    substituted with one -LK-$R^3$.

In more preferred embodiments, each $R^1$ is independently aryl or heteroaryl, preferably aryl, more preferably phenyl, all of which being:
  unsubstituted or substituted with one or more (preferably one) —$R^2$, —$OR^2$, —$P(R^2)_2$, —$SR^2$, —$O$—$CO$—$R^2$, —CO—O—R², —CO—R², —CO—N(R²)₂, —N(R²)₂, —NR²—CO—R², —C=NR², —C≡N, —NO₂, —N₃, halogen, or -LK-R³;
preferably unsubstituted or substituted with one or more (preferably one) —R² or -LK-R³,
more preferably unsubstituted or substituted with one -LK-R³;
yet more preferably either of:
unsubstituted,
substituted with one —R²,
substituted with one —N(R²)₂, or
substituted with one -LK-R³.
In alternative more preferred embodiments:
one or more, preferably one, R¹ group is alkyl, alkenyl, alkynyl, or alkenynyl, preferably alkyl, and more preferably C₅-C₁₂ alkyl, all of which being unsubstituted or substituted as described above, preferably unsubstituted, and
the remaining R¹ groups are aryl or heteroaryl, preferably aryl, more preferably phenyl, all of which being unsubstituted or substituted as described above, preferably unsubstituted.
In other more preferred embodiments, each R¹ is independently aryl or heteroaryl, preferably aryl, more preferably phenyl, wherein:
one, two, three, or all of the aryl and/or heteroaryl are substituted as described above, preferably substituted with one or more —R², and more preferably substituted with one —R², and
the remaining aryl and/or heteroaryl are unsubstituted.
In preferred such embodiments, two, three or all of the aryl and/or heteroaryl are so substituted, more preferably three or all of the aryl and/or heteroaryl are so substituted, and yet more preferably all of the aryl and/or heteroaryl are so substituted.
In alternative preferred embodiments:
one or two R¹ are halogen, preferably F, and
the remaining R¹ are aryl or heteroaryl, preferably aryl, more preferably phenyl, all of which being unsubstituted or substituted as described above, preferably unsubstituted.
In yet other preferred embodiments,
two R¹ together with the boron atom to which they are attached form a:
cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl,
preferably heterocycloalkyl,
more preferably 1,3,2-oxazaborolidin-3-ium-2-uidyl (i.e.

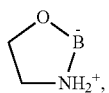

wherein the dot represent the point of attachment of the two other groups (i.e. the Cat⁺-LK- and/or the remaining R¹) on the boron atom), all of which being:
unsubstituted or substituted with one or more of the following: —R², —OR², —P(R²)₂, —SR², —O—CO—R², —CO—O—R², —CO—R², —CO—N(R²)₂, —N(R²)₂, —NR²—CO—R², —C=NR², —C≡N,2019-09-06 —NO₂, —N₃, halogen, or -LK-R³,
preferably unsubstituted, and
each of the remaining R¹ is independently:
alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl,
preferably aryl or heteroaryl,
more preferably aryl,
yet more preferably phenyl,
all of which being:
unsubstituted or substituted with one or more of the following: —R², —OR², —P(R²)₂, —SR², —O—CO—R², —CO—O—R², —CO—R², —CO—N(R²)₂, —N(R²)₂, —NR²—CO—R², —C=NR², —C≡N, —NO₂, —N₃, halogen, or -LK-R³,
preferably unsubstituted.
In preferred embodiments (especially in those embodiments in which R¹ is a group substituted with —R²), R² is alkyl (preferably C₁-C₆ alkyl, more preferably methyl), alkenyl, alkynyl, alkenynyl, a halogen atom (preferably F or I), or —C≡N. In more preferred embodiments, R² is alkyl (preferably C1-C₆ alkyl, more preferably methyl), halogen (preferably F or I, more preferably F), or —C≡N. In yet more preferred embodiments, R² is halogen.
In alternative preferred embodiments, R² is aryl or heteroaryl, preferably heteroaryl, preferably benzimidazol-1-yl, more preferably benzimidazol-1-yl (i.e.

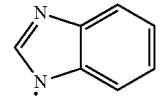

wherein the dot denotes the point of attachment), all of which being:
unsubstituted or substituted with one or more of the following: —R⁴, —OR⁴, —P(R⁴)₂, —SR⁴, —O—CO—R⁴, —CO—O—R⁴, —CO—R⁴, —CO—N(R⁴)₂, —N(R⁴)₂, —NR⁴—CO—R⁴, —C=NR⁴, —C≡N, —NO₂, —N₃, halogen, or -LK-R³,
preferably unsubstituted or substituted with one of the following: —R⁴, —OR⁴, —P(R⁴)₂, —SR⁴, —O—CO—R⁴, —CO—O—R⁴, —CO—R⁴, —CO—N(R⁴)₂, —N(R⁴)₂, —NR⁴—CO—R⁴, —C=NR⁴, —C≡N, —NO₂, —N₃, halogen, or -LK-R³,
more preferably substituted with one of the following: —R⁴, —OR⁴, —P(R⁴)₂, —SR⁴, —O—CO—R⁴, —CO—O—R⁴, —CO—R⁴, —CO—N(R⁴)₂, —N(R⁴)₂, —NR⁴—CO—R⁴, —C=NR⁴, —C≡N, —NO₂, —N₃, halogen, or -LK-R³,
yet more preferably substituted with one —P(R⁴)₂.
In yet other preferred embodiments (especially in those embodiments in which R² is part of the group —N(R²)₂), R² is:
—H, aryl or heteroaryl,
preferably one R² is —H and the other R² is aryl or heteroaryl,
wherein the aryl or heteroaryl is preferably aryl, more preferably naphthyl, and wherein the aryl and/or heteroaryl are:
unsubstituted or substituted with one or more of the following: —R⁴, —OR⁴, —P(R⁴)₂, —SR⁴, —O—CO—R$^4$, —CO—O—R$^4$, —CO—R$^4$, —CO—N(R$^4$)$_2$, —N(R$^4$)$_2$, —NR$^4$—CO—R$^4$, —C=NR$^4$, —C≡N, —NO$_2$, —N$_3$, halogen, or -LK-R$^3$, preferably unsubstituted or substituted with one of the following: —R$^4$, —OR$^4$, —P(R$^4$)$_2$, —SR$^4$, —O—CO—R$^4$, —CO—O—R$^4$, —CO—R$^4$, —CO—N(R$^4$)$_2$, —N(R$^4$)$_2$, —NR$^4$—CO—R$^4$, —C=NR$^4$, —C≡N, —NO$_2$, —N$_3$, halogen, or -LK-R$^3$, more preferably substituted with one of the following: —R$^4$, —OR$^4$, —P(R$^4$)$_2$, —SR$^4$, —O—CO—R$^4$, —CO—O—R$^4$, —CO—R$^4$, —CO—N(R$^4$)$_2$, —N(R$^4$)$_2$, —NR$^4$—CO—R$^4$, —C=NR$^4$, —C≡N, —NO$_2$, —N$_3$, halogen, or -LK-R$^3$, yet more preferably substituted with one —OR$^4$.

In embodiments (especially in those embodiments in which R$^4$ is part of the group —OR$^4$), R$^4$ is H.

In embodiments (especially in those embodiments in which R$^4$ is part of the group —P(R$^4$)$_2$), R$^4$ is aryl or heteroaryl, preferably aryl, more preferably phenyl.

In embodiments, -LK- represents a covalent bond or one or more of the following, alone or in combination, amide, amine, imine, —C(=O)—, —S—, —S—S—, —O—, ester, alkylene, alkenylene, alkynylene, alkenylnylene, cycloalkylene, cycloalkenylene, cycloalkynylene, cycloalkenynylene, heterocycloalkylene, heterocycloalkenylene, heterocycloalkynylene, heterocycloalkenynylene, arylene, or heteroarylene.

An example of -LK- is alkylene combined with —O— to form, for example, one or more alkyleneoxy groups, preferably one or more ethyleneoxy: —(CH$_2$—CH$_2$—O)$_q$—, wherein q is 1 or more, for example 1, 2, or 3.

Another example of -LK- is heteroarylene, for example triazolylene, preferably 1,2,3-triazolylene, and more preferably 1,2,3-triazol-1,4-ylene

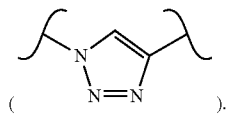

The heteroarylene may be alone or combined with one or more alkylene, alkenylene, alkynylene, or alkenylnylene groups, preferably two such groups, more preferably one such group on each side of the heteroarylene. One such -LK- group comprises methylene group(s), preferably one on each side of the heteroarylene. For example, the -LK- can be:

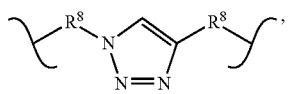

wherein each R$^8$ is independently alkylene, alkenylene, alkynylene, or alkenylnylene, preferably alkylene, more preferably methylene.

Another example of -LK- is arylene, for example phenylene, preferably paraphenylene (i.e.

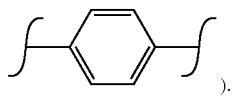).

The arylene may be alone or combined with one or more (preferably one) alkylene, alkenylene, alkynylene, or alkenylnylene groups, preferably alkylene, more preferably methylene. For example, the -LK- can be:

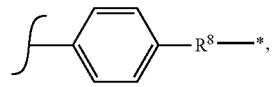

wherein * denotes the point of attachment of R$^3$ and wherein R$^8$ is independently alkylene, alkenylene, alkynylene, or alkenylnylene, preferably alkylene, more preferably methylene.

In preferred embodiments, -LK- represents a covalent bond or one or more of the following, alone or in combination, —O—, alkylene, alkenylene, alkynylene, alkenylnylene, or heteroarylene.

In more preferred embodiments, -LK- represents a covalent bond.

As noted above, R$^3$ is a pharmaceutically acceptable compound. Herein, "pharmaceutically acceptable compound" is a compound that is substantially non-toxic to the subject to which it is administered. More specifically, the compound may be pharmaceutically inactive or be pharmaceutically active (i.e. have a biological effect and/or therapeutic properties).

Preferred pharmaceutically acceptable compounds include pharmaceutically active compounds.

Preferred pharmaceutically active compounds include antibiotics conventionally used against *Neisseria* or that have been reported as promising candidates for this use, including for example quinolone antibiotics (e.g. ciprofloxacin), cephalosporin antibiotics (e.g., ceftriaxone, cefixime, cefotaxime), tetracyclin, erythromycin, penicillin (e.g., penicillin G), chloramphenicol, azithromycin, spectinomycin, doxycycline, gemifloxacin, or gentamicin.

Alternative pharmaceutically acceptable compounds include metal-based complexes, such as ruthenium complexes, which may or may be pharmaceutically active. In preferred embodiments, R$^3$ represents a ruthenium complex, such as:

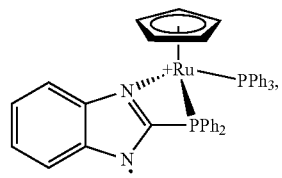

wherein the dot represents the point of attachment.

As noted above, Cat$^+$ represents pharmaceutically acceptable cations. Herein, a "pharmaceutically acceptable cation" is a positively charged ion that is pharmaceutically acceptable, i.e. that is substantially non-toxic to the subject to which it is administered. More specifically, the compound may be pharmaceutically inactive or be pharmaceutically active (i.e. have a biological effect and/or therapeutic properties). Pharmaceutically active cations may be, for example, pharmaceutically active compounds that bear a positive charge, or bear a functional group that has been protonated, for example an amine functional group, to create a positive charge.

Preferred pharmaceutically acceptable cations include pharmaceutically inactive cations. Such cations are very well known and documented. Non-limiting examples of such cations include alkali metal cations such as $Na^+$, $Li^+$, and $K^+$; alkaline earth metal cations such as $Ca^{2+}$ and $Mg^{2+}$; metal cations such as aluminum, iron, zinc, copper, nickel and cobalt cations; inorganic amine cations such as ammonium ($NH_4^+$) or substituted ammonium cations such as e.g. ethyl ammonium, diethylammonium, trimethylammonium tetraethylammonium, tetramethylammonium and tetrabutylammonium cations; and cations of organic bases (for example, organic amines) such as chloroprocaine, dibenzylamine, dicyclohexylamine, dicyclohexylamines, diethanolamine, ethylamine (including diethylamine and triethylamine), ethylenediamine, glucosamine, guanidine, methylamine (including dimethylamine and trimethylamine), morpholine, choline, N,N'-dibenzylethylenediamine, N-benzyl-phenethylamine, N-methylglucamine, phenylglycine alkyl ester, piperazine, piperidine, procaine, t-butyl amines, tetramethylammonium, t-octylamine, tris-(2-hydroxyethyl)amine, and tris(hydroxymethyl)aminomethane cations.

In most preferred embodiments, the pharmaceutically acceptable cation is $Na^+$, $K^+$, or $NH_4^+$.

Alternative pharmaceutically acceptable cations include cationic metal-based complexes, such as cationic ruthenium complexes, which may or may be pharmaceutically active. In preferred embodiments, the pharmaceutically acceptable cations include is a cationic ruthenium complex, such as:

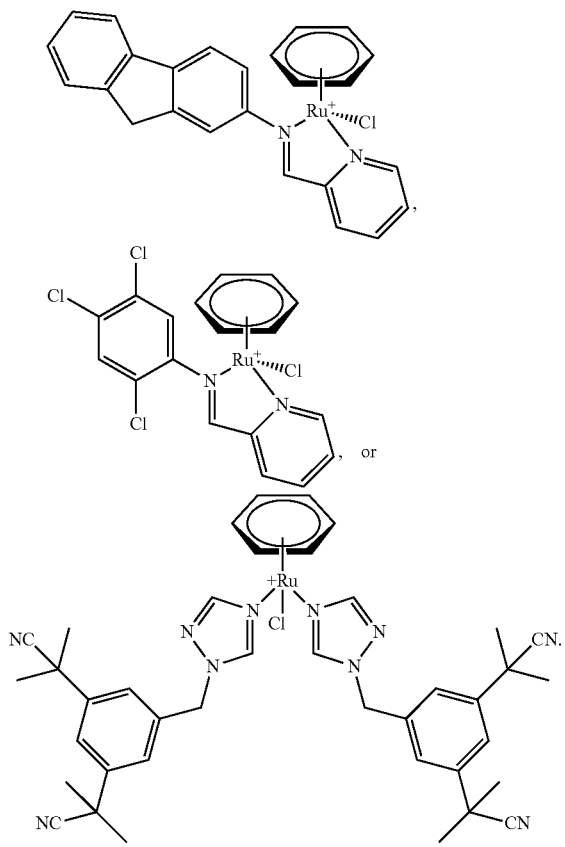

Herein, a pharmaceutically acceptable anion is negatively charged ion that is pharmaceutically acceptable. Pharmaceutically acceptable anions are very well known and documented. Non-limiting examples of such anions include aceglutamate, acephyllinate, acetamidobenzoate, acetate, acetylasparaginate, acetylaspartate, adipate, aminosalicylate, anhydromethylenecitrate, ascorbate, aspartate, benzoate, benzylate, besylate, bicarbonate, bisulphate, bitartrate, borate, bromide, butylbromide, camphorate, camsylate, carbonate, chloride, chlorophemoxyacetate, citrate, closylate, cromesilate, cyclamate, dehydrochloate, dihydrochloride, dimalonate, edetate, edisylate, estolate, esylate, ethylbromide, ethylsulfate, fendizoate, fluoride, formate, fosfatex, fumarate, gluceptate, gluconate, glucoronate, glutamate, glycerophosphate, glycinate, glycollylarsinilate, glycyrrhizate, hippurate, hemisulphate, hexylresorcinate, hybenzate, hydrobromide, hydrochloride, hydroiodide, hydroxybenzenesulfonate, hydroxybenzoate, iodide, isethionate, lactate, lactobionate, lysine, malate, maleate, mandalate, mesylate, methylbromide, methyliodide, methylnitrate, methylsulphate, monophosadenine, mucate, napadisylate, napsylate, nicotinate, nitrate, oleate, orotate, oxalate, oxoglurate, pamoate, pantothenate, pectinate, phenylethylbarbiturate, phosphate, picrate, policrilix, polistirex, pyridoxylphosphate, polygalacturonate, propionate, saccharinate, salicylate, stearate, stearylsulphate, subacetate, succinate, sulfate, sulfosalicylate, tannate, tartrate, teprosilate, terephthalate, teoclate, thiocyanate, timonaciate, tosylate, triethiodide, undecanoate, and xinafoate. Preferred anions include acetate, besylate, bisulphate, bromide, carbonate, chloride, citrate, fluoride, formate, iodide, maleate, mesylate, methylsulphate, nitrate, nitrite, pamoate, phosphate, stearate, sulfate, and tartrate.

In more preferred embodiments, the borate compound is of formula:

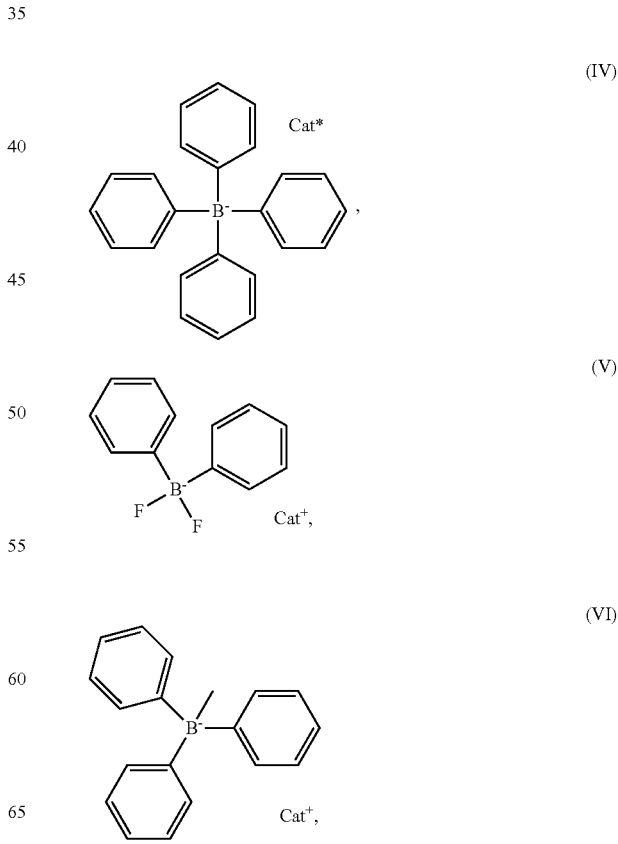

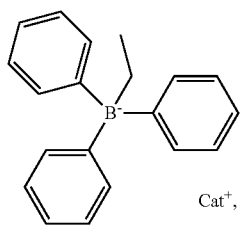
(VII)
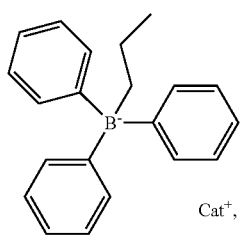
(VIII)
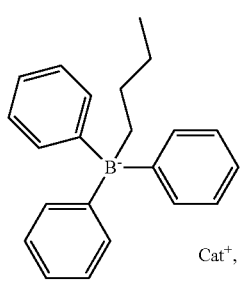
(IX)
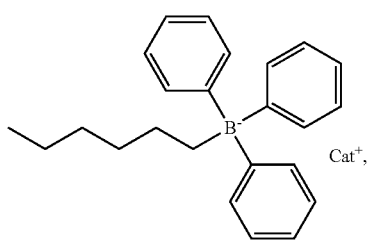
(X)
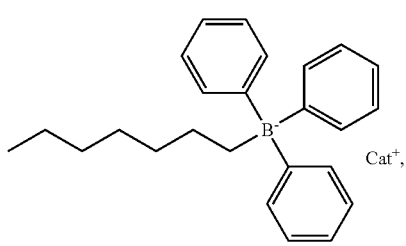
(XI)
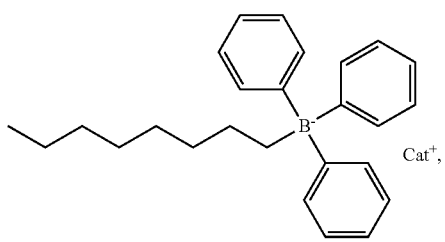
(XII)
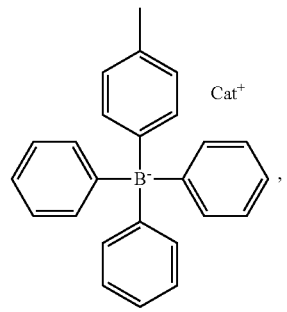
(XIII)
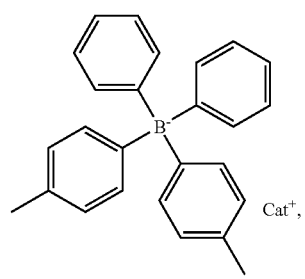
(XIV)
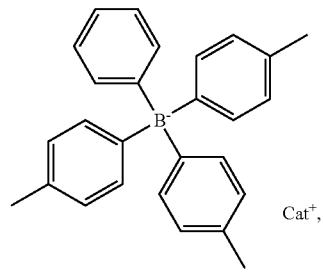
(XV)
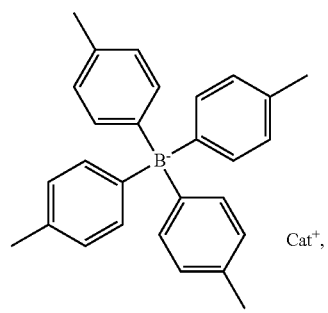
(XVI)
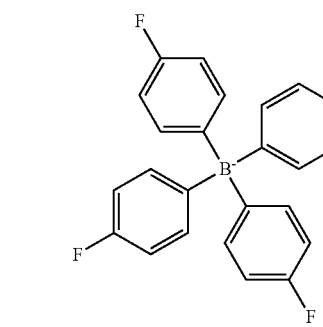
(XVII)

-continued
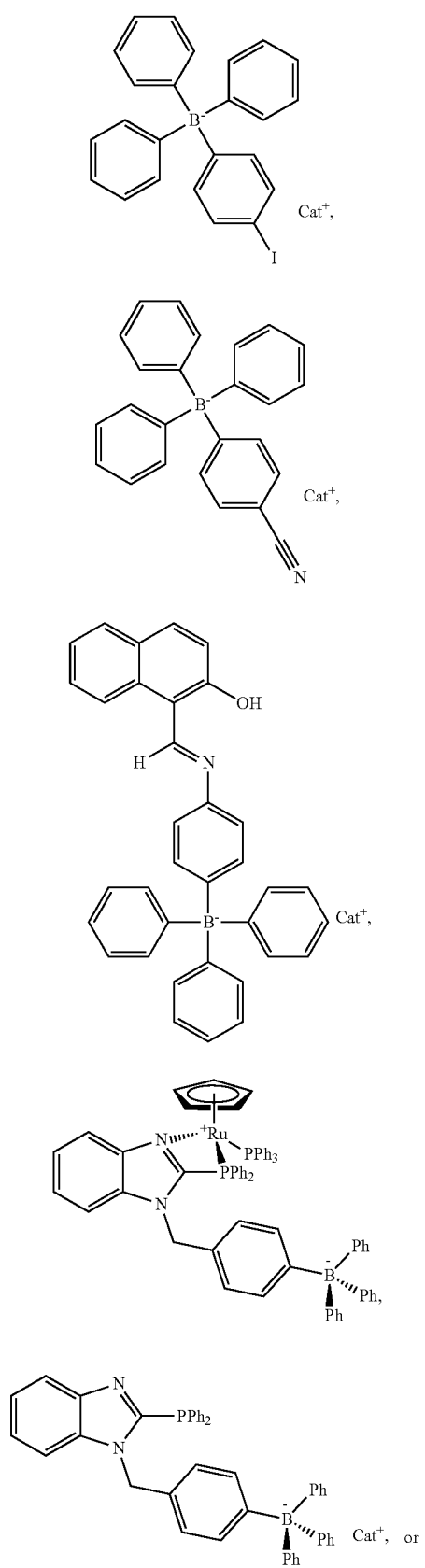
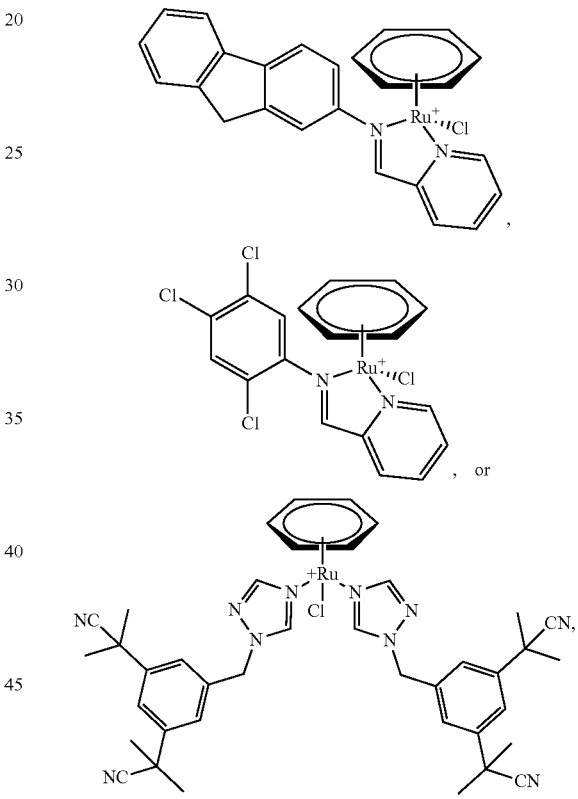
preferably the borate compound is of formula (IV)-(XXII), more preferably of formula (VIII)-(XII), (XIV)-(XVIII), or (XX)-(XXII), and most preferably of formula (X)-(XII), (XXI), or (XXII),
wherein $Cat^+$ is as defined above and is preferably $Na^+$, $K^+$, $NH_4^+$,
and more preferably
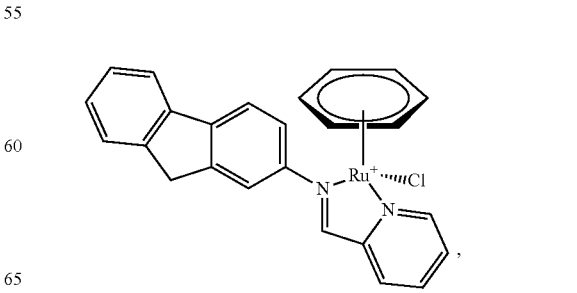

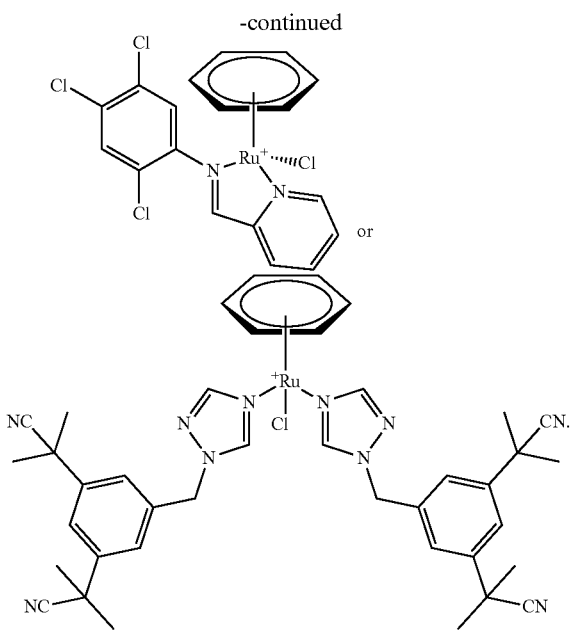

or

Generally, more preferred compounds have a relatively higher lipophilicity, preferably with a log $P_{octanol/water}$ of 0 or more, preferably 0.5 or more, more preferably 1 or more, yet more preferably 1.5 or more, and most preferably 2 of more.

As well-known to the skilled person, when expressing lipophilicity as log P, P is the partition coefficient; that is the ratio of the concentrations of the compound between a hydrophobic phase and a hydrophilic phase (forming a biphasic liquid mixture), generally water and octanol.

$$\log P_{octanol/water} = \log \frac{[\text{compound}]_{octanol}}{[\text{compound}]_{water}}$$

The measurement of log P is well described in the literature—see e.g. Román, I. P.; Mastromichali, A.; Tyrovola, K.; Canals, A.; Psillakis, E. Rapid Determination of Octanol-Water Partition Coefficient Using Vortex-Assisted Liquid-Liquid Microextraction. J. Chromatogr. A 2014, 1330, 1-5; and Yiantzi, E.; Psillakis, E.; Tyrovola, K.; Kalogerakis, N. Vortex-Assisted Liquid-Liquid Microextraction of Octylphenol, Nonylphenol and Bisphenol-A. Talanta 2010, 80 (5), 2057-2062, both of which are incorporated herein by reference.

In an embodiment, the treatment results in the selective growth inhibition and/or killing of pathogenic Neisseria bacteria. "Selective" as used herein means that the compound is more effective or potent at inhibiting the growth and/or killing pathogenic Neisseria species relative to other bacteria, and more particularly non-pathogenic Neisseria species. Accordingly, a lower concentration of the compound is needed to induce a similar inhibition of the growth and/or killing of pathogenic Neisseria bacteria relative to other bacteria, or the same concentration of compound will induce more growth inhibition and/or killing in pathogenic Neisseria bacteria relative to other bacteria, and more particularly non-pathogenic Neisseria species.

The term "pathogenic Neisseria bacteria" or "pathogenic Neisseria species" as used herein refers to Neisseria species that cause a disease in the infected subject (e.g., human), for example N. meningitidis and N. gonorrhoeae. In an embodiment, the pathogenic Neisseria bacteria or species is N. meningitidis. In an embodiment, the pathogenic Neisseria bacteria or species is N. gonorrhoeae. In an embodiment, the pathogenic Neisseria bacteria is resistant to one or more antibiotics, for example one or more antibiotics currently used for the treatment of infections by the pathogenic Neisseria bacteria. In an embodiment, the pathogenic Neisseria bacteria is resistant to a cephalosporin antibiotic (e.g., ceftriaxone, cefixime, and/or cefotaxime), penicillin (e.g., penicillin G or benzylpenicillin), chloramphenicol, azithromycin, spectinomycin, doxycycline, gemifloxacin and/or gentamicin.

The term "non-pathogenic Neisseria bacteria" or "non-pathogenic Neisseria species" refers to Neisseria bacteria or species that are components of the normal microbiome, and which do not cause a disease in non-immunocompromised or non-immunosuppressed hosts. Thus, Neisseria species that only cause opportunistic infections in immunocompromised or immunosuppressed individuals are considered non-pathogenic Neisseria species. Examples of non-pathogenic Neisseria bacteria include N. polysaccharea, N. lactamica, N. cinereal, N. skkuensis, N. sicca, N. mucosa, N. flavescens, N. subflava, N. elongate, and N. bacilliformis. In an embodiment, the treatment with the compound does not induce significant growth inhibition and/or killing in non-pathogenic Neisseria bacteria.

In an embodiment, the borate compound as described herein is present in a composition, preferably a pharmaceutical composition. Such composition comprises, in addition to the borate compound, a carrier or excipient, preferably a pharmaceutically acceptable carrier or excipient.

An "excipient," as used herein, has its normal meaning in the art and is any ingredient that is not an active ingredient (drug) itself. Excipients include for example binders, lubricants, diluents, fillers, thickening agents, disintegrants, plasticizers, coatings, barrier layer formulations, lubricants, stabilizing agent, release-delaying agents and other components. "Pharmaceutically acceptable excipient" as used herein refers to any excipient that does not interfere with effectiveness of the biological activity of the active ingredients and that is not toxic to the subject, i.e., is a type of excipient and/or is for use in an amount which is not toxic to the subject. Excipients are well known in the art, and the present composition is not limited in these respects. In certain embodiments, the composition may include, for example and without limitation, one or more binders (binding agents), thickening agents, surfactants, diluents, release-delaying agents, colorants, flavoring agents, fillers, disintegrants/dissolution promoting agents, lubricants, plasticizers, silica flow conditioners, glidants, anti-caking agents, anti-tacking agents, stabilizing agents, anti-static agents, swelling agents and any combinations thereof. As those of skill would recognize, a single excipient can fulfill more than two functions at once, e.g., can act as both a binding agent and a thickening agent. As those of skill will also recognize, these terms are not necessarily mutually exclusive.

Supplementary active compounds can also be incorporated into the compositions. The carrier/excipient can be suitable, for example, for intravenous, parenteral, subcutaneous, intramuscular, intracranial, intraorbital, ophthalmic, intraventricular, intravaginal, intracapsular, intraspinal, intrathecal, epidural, intracisternal, intraperitoneal, intranasal or pulmonary (e.g., aerosol) administration. Such compositions may be prepared in a manner well known in the pharmaceutical art by mixing the active ingredient having the desired degree of purity with one or more optional pharmaceutically acceptable carriers and/or excipients (see, e.g., Remington: The Science and Practice of Pharmacy, by Loyd V Allen, Jr, 2012, 22$^{nd}$ edition, Pharmaceutical Press Handbook of Pharmaceutical Excipients, by Rowe et al., 2012, 7$^{th}$ edition, Pharmaceutical Press).

Any suitable amount of the compound or composition comprising same may be used or administered to a subject. The dosages will depend on many factors including the mode of administration. Typically, the amount of the borate compound, or composition comprising same, contained within a single dose will be an amount that effectively inhibits the growth and/or kills pathogenic *Neisseria* bacteria, or treats the pathogenic *Neisseria* infection in a subject, without inducing significant toxicity.

For the treatment or reduction in the severity of a given disease or condition, the appropriate dosage of the compound/composition will depend on the type of disease or condition to be treated, the severity and course of the disease or condition, whether the compound/composition is administered for preventive or therapeutic purposes, previous therapy, the patient's clinical history and response to the compound/composition, and the discretion of the attending physician. The compound/composition is suitably administered to the patient at one time or over a series of treatments. Preferably, it is desirable to determine the dose-response curve in vitro, and then in useful animal models prior to testing in humans. The present invention provides dosages for the compounds and compositions comprising same. For example, depending on the type and severity of the disease, about 1 µg/kg to 1000 mg per kg (mg/kg) of body weight per day. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, and may increase by 25 mg/kg increments up to 1000 mg/kg, or may range between any two of the foregoing values. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

In an embodiment, the borate compound, or composition comprising same, as described herein is used in combination with another agent (e.g., an antibiotic) for inhibiting the growth and/or killing pathogenic *Neisseria* bacteria, or for treating a pathogenic *Neisseria* infection in a subject. The combination of agents and/or compositions of the present disclosure may be administered or co-administered (e.g., consecutively, simultaneously, at different times) in any conventional dosage form. Co-administration in the context of the present disclosure refers to the administration of more than one therapeutic agent in the course of a coordinated treatment to achieve an improved clinical outcome (e.g., reduction of the pathogenic *Neisseria* bacteria burden, reduction of one or more of the symptoms of the pathogenic *Neisseria* infection). Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) is used/administered in combination with one or more agent(s) currently used to prevent or treat the disease in question. In an embodiment, the borate compound is used in combination with one or more antibiotics, more particularly antibiotics used for the treatment of pathogenic *Neisseria* bacterial infection. Examples of antibiotics used for the treatment of *N. gonorrhoeae* and/or *N. meningitidis* include cephalosporin antibiotics (e.g., ceftriaxone, cefixime, cefotaxime), penicillin (e.g., penicillin G), chloramphenicol, azithromycin, spectinomycin, doxycycline, gemifloxacin and/or gentamicin. In an embodiment, the borate compound is used with a combination of antibiotics, e.g., (1) a cephalosporin antibiotic (e.g., ceftriaxone, cefotaxime) and (2) azithromycin or doxycycline.

In an embodiment, the dose of the borate compound and/or of the one or more antibiotics that is used/administered in the methods, uses, compositions and combinations of the disclosure is a suboptimal dose. "Suboptimal dose" as used herein refers to a dose of one of the compounds of the combination described herein, which, when used in the absence of another compound of the combination, results in a biological effect (e.g. inhibition of bacterial growth and/or killing) of less than 100%, for example 90% or less, 80% or less, 70% or less, 60% or less, 50% or less, 40% or less, 30% or less, 20% or less, or 10% or less. As such, use of a combination of the compounds described herein, where one or more compounds in the combination is used at a suboptimal dose, may achieve increased efficacy/biological effect relative to using the compound(s) in the absence of the other(s), at a comparable suboptimal dose. The use of suboptimal doses may permit to reduce the side effects or toxicity of the compounds without affecting the efficacy of the treatment.

The borate compounds of the invention can be prepared, for example by first preparing a R-functionalized $BPh_4^-$ ion ($[B(PhR)Ph_3]^-$, where R=halogen, amine, alkyne, azide, aldehyde, hydroxyl, etc.) (example shown in Scheme 1A below), and allow it to react with a pharmaceutically active compound of interest (as well known to a skilled person, the protection/deprotection of some of its functional groups may be required). For instance, amine-containing pharmaceutically active compounds (such as ciprofloxacin) could directly react with $[B(PhBr)Ph_3]^-$ (no pharmaceutically active compound modification necessary) via a metal-catalyzed cross-coupling reaction, such as the Hartwig-Buckwald amination (Scheme 1A). Amine-containing pharmaceutically active compounds can also react with $[B(PhCHO)Ph_3]^-$, leading to the formation of an imine Schiff base. Some pharmaceutically active compounds containing carboxylic acid moieties can also undergo an esterification reaction with $[B(PhOH)Ph_3]^-$, leading to an hydrolyzable prodrug candidate.

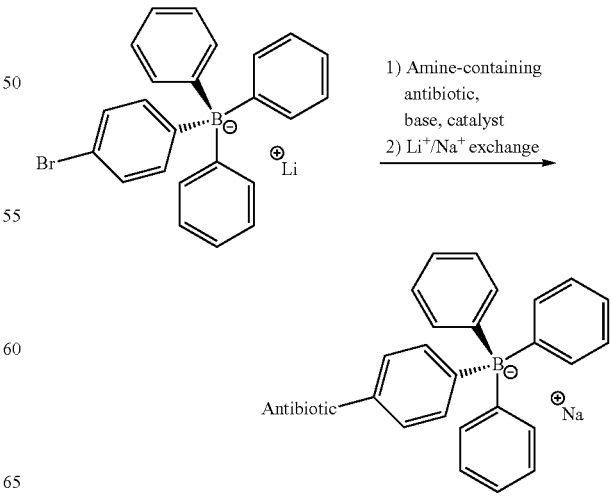

Scheme 1A-Direct functionalization

Another approach uses the versatile Cu-catalyzed alkyne azide cycloaddition (CuAAC, known as click chemistry), which requires the functionalization of both the pharmaceutically active compound and the borate motif with a terminal alkyne or an azide (examples shown in Scheme 1B). In some cases, the pharmaceutically active compound is directly functionalized with a terminal alkyne or an azide, whereas in other cases, it has to be synthetized using a functionalized building block to allow the incorporation of the selected CuAAC partner.

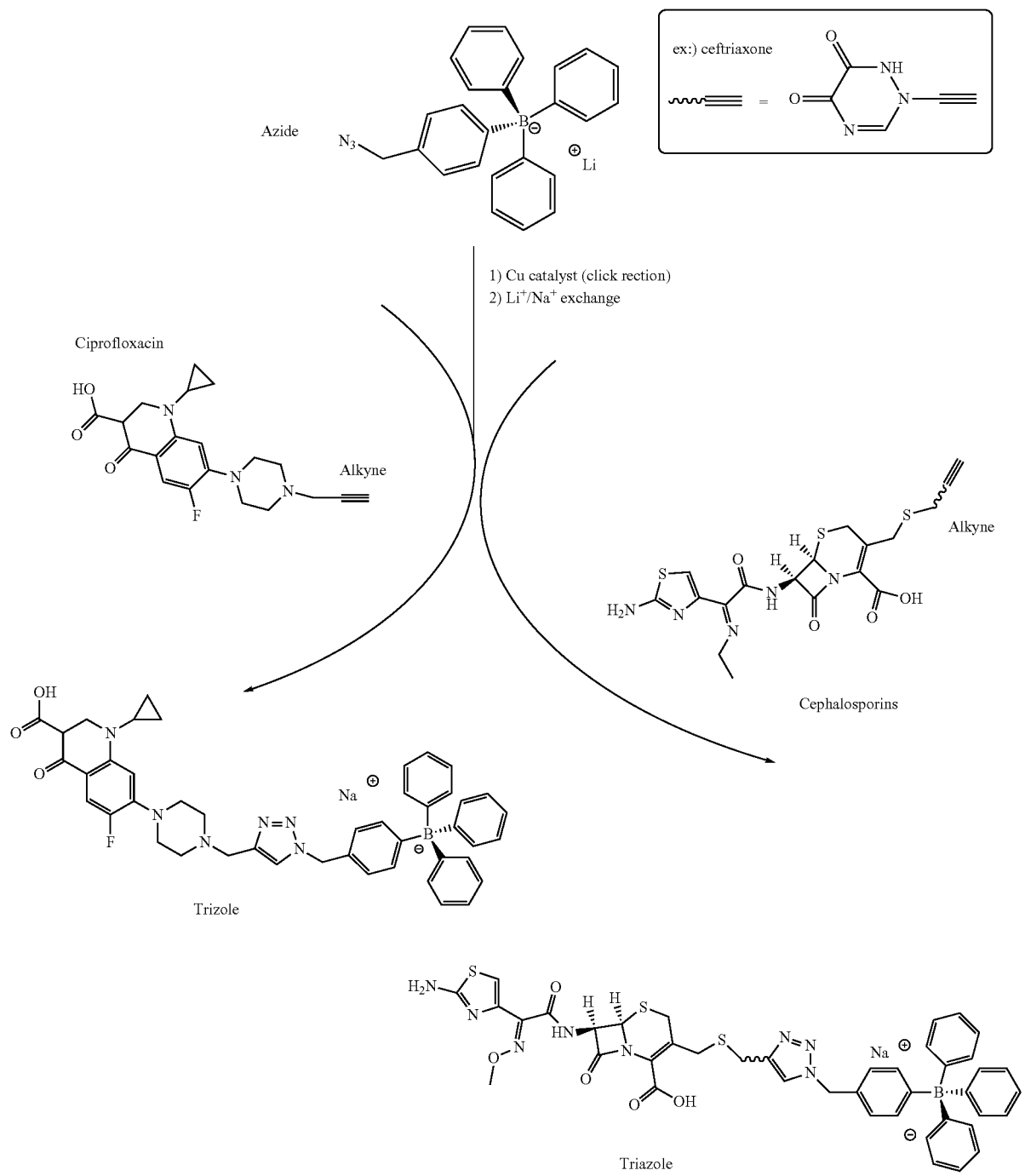

An example of the formation of a zwitterionic structure of formula (III) is shown in Scheme 1C, where the pharmacologically active compound is a metal-based species.

Scheme 1C-Formation of a formula (III)-type zwitterionic structure

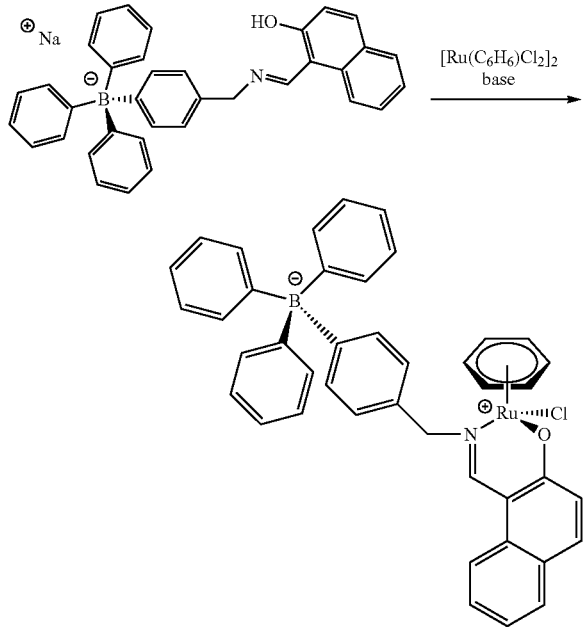

Definitions

The use of the terms "a" and "an" and "the" and similar referents in the context of describing the invention (especially in the context of the following claims) are to be construed to cover both the singular and the plural, unless otherwise indicated herein or clearly contradicted by context.

The terms "comprising", "having", "including", and "containing" are to be construed as open-ended terms (i.e., meaning "including, but not limited to") unless otherwise noted.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

Similarly, herein a general chemical structure, such as Formulas (I) to (III), with various substituents ($R^1$, $R^2$, etc.) and various radicals (alkyl, halogen atom, etc.) enumerated for these substituents is intended to serve as a shorthand method of referring individually to each and every molecule obtained by the combination of any of the radicals for any of the substituents. Each individual molecule is incorporated into the specification as if it were individually recited herein. Further, all subsets of molecules within the general chemical structures are also incorporated into the specification as if they were individually recited herein.

The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

Unless otherwise defined, all technical and scientific terms used herein have the same meaning as commonly understood by one of ordinary skill in the art to which this invention belongs.

Herein, the "alkyl", "alkenyl", "alkynyl", "alkenynyl", "alkylene", "alkenylene", "alkynylene", and "alkenylnylene", as well as their derivatives (such as alkoxy, alkyleneoxy, etc.) have their ordinary meaning in the art. For more certainty, herein:

| Term | Definition |
| --- | --- |
| alkyl | monovalent saturated aliphatic hydrocarbon radical of general formula —$C_nH_{2n+1}$ |
| alkenyl | monovalent aliphatic hydrocarbon radical similar to an alkyl, but comprising at least one double bond |
| alkynyl | monovalent aliphatic hydrocarbon radical similar to an alkyl, but comprising at least one triple bond |
| alkenynyl | monovalent aliphatic hydrocarbon radical similar to an alkyl, but comprising at least one double bond and at least one triple bond |
| alkylene | bivalent saturated aliphatic hydrocarbon radical of general formula —$C_nH_{2n}$- (also called alkanediyl) |
| alkenylene, alkynylene, alkenynylene | bivalent aliphatic hydrocarbon radical similar to an alkylene, but comprising, respectively, at least one double bond, at least one triple bond, and at least one double bond and at least one triple bond |
| alkyloxy or alkoxy | monovalent radical of formula -O-alkyl |
| alkyleneoxy | bivalent radical of formula -O-alkylene-. An example of alkyleneoxy is —O—$CH_2$—$CH_2$—, which is called ethyleneoxy. A linear chain comprising two or more ethyleneoxy groups attached together (i.e. —[O—$CH_2$—$CH_2$]n-) can be referred to as a polyethylene glycol (PEG), polyethylene oxide (PEO), or polyoxyethylene (POE) chain. |
| alkenyloxy, alkenyleneoxy, alkynyloxy, alkynyleneoxy | monovalent radical of formula -O-alkenyl, -O-alkenylene, -O-alkynyl, and -O-alkynylene, respectively |

It is to be noted at, unless otherwise specified, the hydrocarbon chains of the above groups can be linear or branched. Further, unless otherwise specified, these groups can contain between 1 and 18 carbon atoms, more specifically between 1 and 12 carbon atoms, between 1 and 6 carbon atoms, between 1 and 3 carbon atoms, or contain 1 or 2, preferably 1, or alternatively preferably 2 carbon atoms.

Herein, the terms "cycloalkyl", "cycloalkenyl", "cycloalkynyl", "cycloalkenynyl", "cycloalkylene", "cycloalkenylene", "cycloalkynylene", "cycloalkenynylene", "heterocycloalkyl", "heterocycloalkenyl", "heterocycloalkynyl", "heterocycloalkenynyl", "aryl", "arylene", "heteroaryl", and "heteroarylene" have their ordinary meaning in the art. For more certainty, herein:

| Term | Definition |
|---|---|
| cycloalkyl | monovalent saturated aliphatic hydrocarbon radical of general formula $C_nH_{2n-1}$, wherein the carbon atoms are arranged in a ring (also called cycle). |
| cycloalkenyl, cycloalkynyl, cycloalkenynyl | monovalent saturated aliphatic hydrocarbon radical similar to cycloalkyl but comprising, respectively, at least one double bond, at least one triple bond, and at least one double bond and at least one triple bond. |
| cycloalkylene | bivalent saturated aliphatic hydrocarbon radical of general formula $-C_nH_{2n}-$, wherein the carbon atoms are arranged in a ring (also called cycle). |
| cycloalkenylene, cycloalkynylene, cycloalkenynylene | bivalent aliphatic hydrocarbon radical similar to cycloalkyl but comprising, respectively, at least one double bond, at least one triple bond, and at least one double bond and at least one triple bond. |
| heterocycloalkyl | cycloalkyl wherein at least one of the carbon atoms is replaced by a heteroatom, such as nitrogen or oxygen. |
| heterocycloalkenyl, heterocycloalkynyl, heterocycloalkenynyl | respectively, cycloalkenyl, cycloalkynyl, and cycloalkenynyl, wherein at least one of the carbon atoms is replaced by a heteroatom, such as nitrogen or oxygen |
| aryl | monovalent aromatic hydrocarbon radical presenting alternating double and single bonds between carbon atoms arranged in one or more rings. |
| arylene | bivalent aromatic hydrocarbon radical presenting alternating double and single bonds between carbon atoms arranged in one or more rings. |
| heteroaryl | aryl wherein at least one of the carbon atoms is replaced by a heteroatom, such as nitrogen or oxygen. |
| heteroarylene | arylene wherein at least one of the carbon atoms is replaced by a heteroatom, such as nitrogen or oxygen. |

It is to be note that, unless otherwise specified, each of the rings of the above groups can comprise between 4 and 8, preferably 5 or 6 ring atoms. It is to be noted that, unless otherwise specified, the above groups can comprise up to 4 rings, preferably 1 or 2 rings, more preferably 1 ring.

Herein, a "group substituted with one or more A, B, and/or C" means that one or more hydrogen atoms of the group may be replaced with groups selected from A, B, and C. Of note, the group do not need to be identical; one hydrogen atom may be replaced by A, while another may be replaced by B.

MODE(S) FOR CARRYING OUT THE INVENTION

The present invention is illustrated in further details by the following non-limiting examples.

Example 1: Materials and Methods

Bacterial Strains and Culture Conditions

All Neisseriaceae strains and *Moraxella catarrhalis* were grown in GCB agar medium with Kellogg supplements. Other strains were grown at 37° C. in Luria-Bertani Media (Difco). For cloning experiments, *E. coli* DH5a was grown at 37° C. in Luria-Bertani Media. When required, the antibiotic erythromycin was added (300 μg/ml for *E. coli*; 3 μg/ml for *Neisseria* sp.). *S. aureus* (33592), *N. elongata* subsp. *glycolytica* (29315), *N. lactamica* (23970), *N. baciliformis* (BAA-1220), *N. sicca* (29256), *K. oralis* (51147) were obtained from the American Type Culture Collection (ATCC). *Y. enterocolitica* DSM23249 was purchased from the Deutsche Sammlung von Mikroorganismen und Zellkulturen GmbH Collection (DSMZ). *M. catarrhalis* LNP18103, *N. meningitidis* LPNP24198 and *N. gonorrhoeae* LNP16626 were obtained from M. K. Taha from the Centre National de Reference des Meningocoques (CNRM, Institut Pasteur, Paris) whereas *C. rodentium* DBS100 was obtained as a donation from Hervé le Moual (McGill University).

*N. meningitidis* Luminescent Strain Growth Assay (16 h)

Figures 1B, 1C:
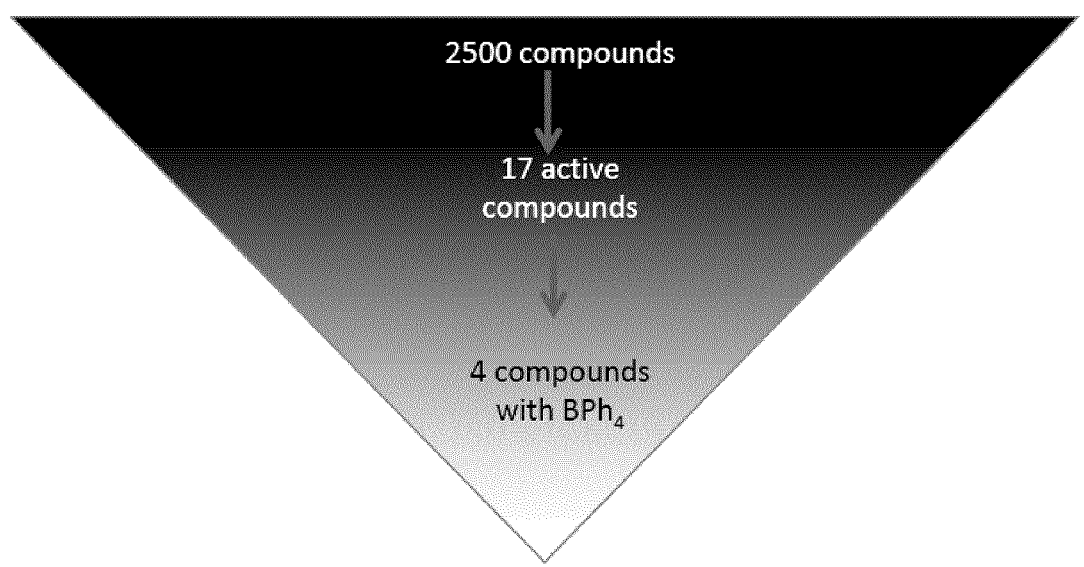
FIG. 1B is a table showing the mean RLU obtained after 16 h of growth for the DMSO 1%, the erythromycin 4 µM and compounds with RLU similar to erythromycin tested at least in triplicates.
FIG. 1C depicts a summary of the library screening results.
Figure 2C:
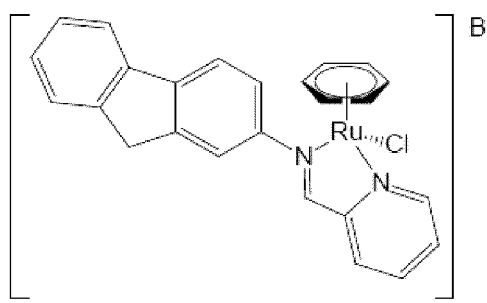
FIG. 2C shows the structure of compounds tested in the studies described herein. Anas=Anastrozole.
Figure 2C:
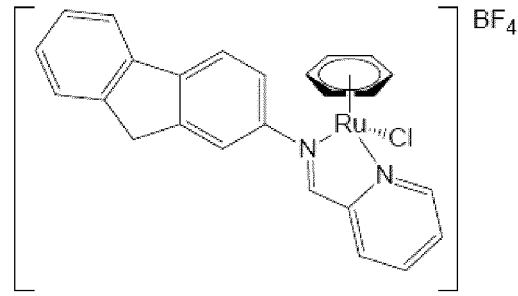
Figure 2C:
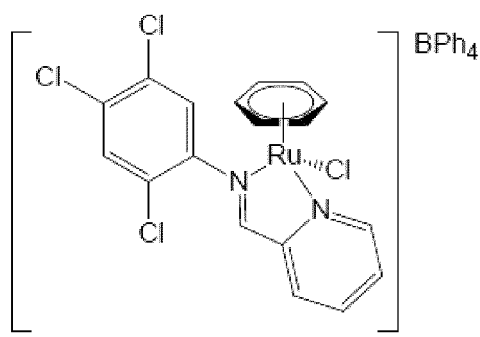
Figure 2C:
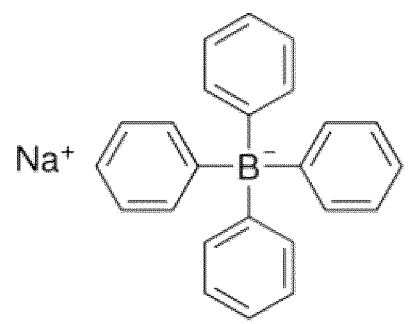
Figure 2C:
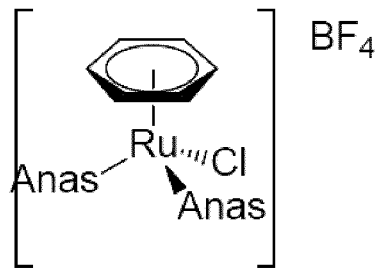
Figure 2C:
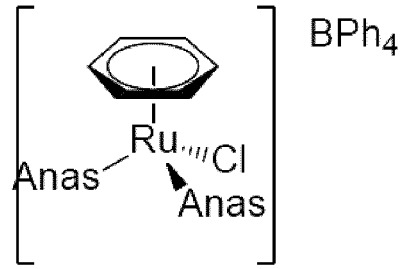
Figure 3:
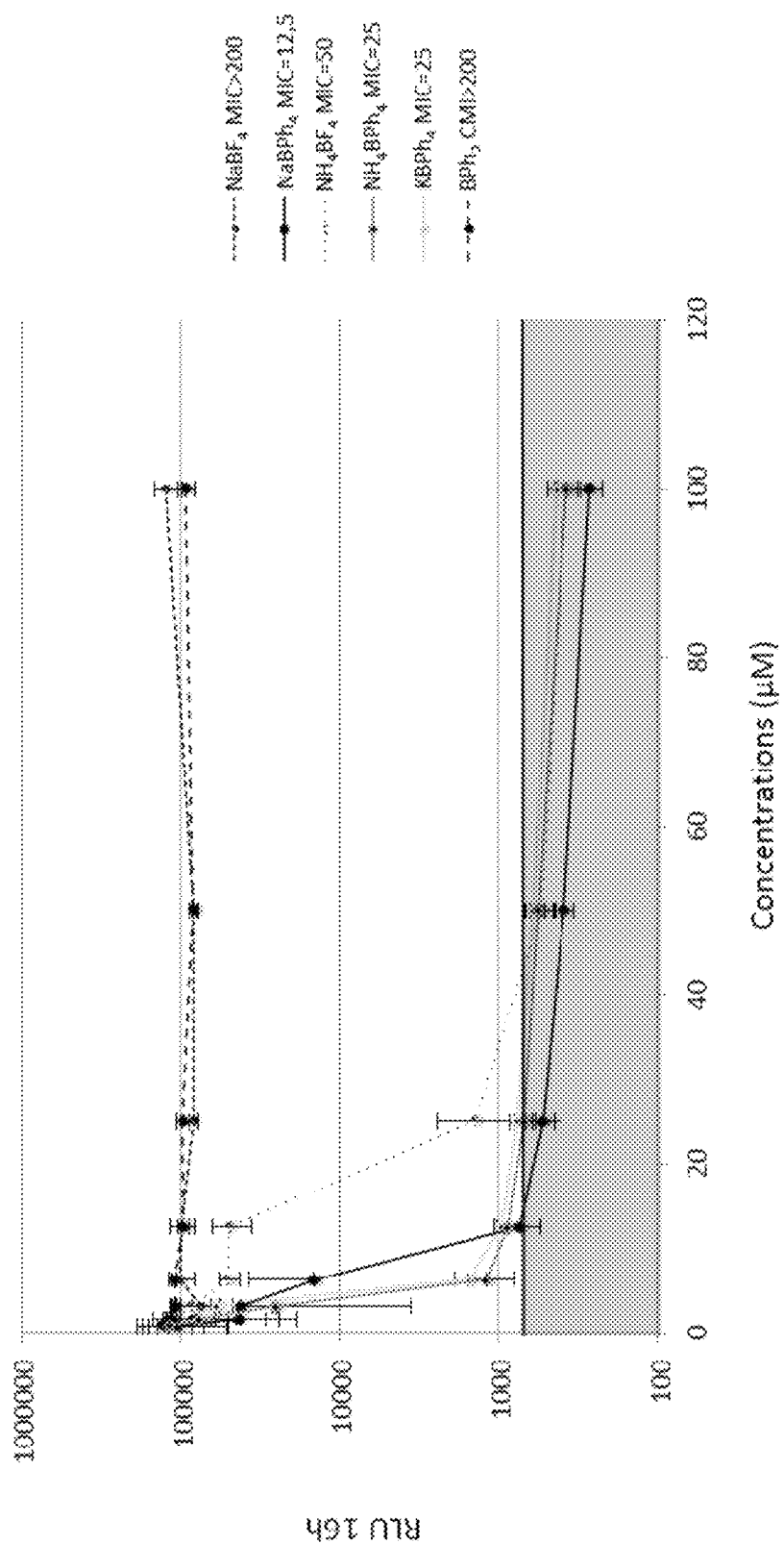
FIG. 3 shows the concentration dependent growth inhibition and minimal inhibitory concentration for different $BPh_4$ and $BF_4$ salts. Each point represents the average of three independent measurements.

To perform the library screening (FIG. 1) or to compare the activity of the different boron-containing salts (FIG. 3), the amount of light produced after 16 h of growth for *N. meningitidis* luminescent strain was measured. Contrarily to optical density (OD) readings which can be misleading due to the absorbance of dead cells, this measurement is directly correlated to the number of live cells, as the half-life of the luciferase and its substrate are limited and that the emission of light is therefore not subsisting after the death of the cells. To perform this assay, *N. meninigitidis* (LNP24198) expressing luciferase (LuxABCDE) was grown overnight under the control of the constitutive promoter porBp in GCB agar media, and a cell-suspension corresponding to an $OD_{600}$=0.01 was subsequently prepared. In parallel, fresh stock DMSO solutions of the compounds were prepared (100×, with final concentrations being indicated in the different figures) and 1.8 μL of the corresponding solutions were added per well of 96-well plates. In each well, 178.2 μL of bacterial suspension were subsequently added. Bacteria were allowed to grow during 16 h at 37° C. with 5% $CO_2$. The emitted light was measured using a 96-well plate luminometer (PerkinElmer Wallac 1420 Victor³) and results are expressed in relative light unit (RLU). All these assays were performed at least in triplicates.

Bacterial Survival Assay (3 h)

To measure bacterial survival (FIGS. 2 and 4), different bacteria were exposed to various concentrations of the compounds (as indicated) in their specific growth media (see the culture conditions above) for 3 h at 37° C. To perform this assay, all strains were grown overnight in their corresponding agar media. Cell-suspension corresponding to an $OD_{600}$=0.05 were subsequently prepared. In parallel, fresh stock DMSO solutions of the compounds were prepared (100×, with final concentrations being indicated in the different figures) and 1.8 μL of the corresponding solutions were added per well of 96-well plates. In each well, 178.2 μL of bacterial suspension were subsequently added. Bacteria were allowed to grow during 16 h at 37° C. with 5% $CO_2$. After incubation, serial dilutions (until $10^{-6}$) were performed and 50 μL of each diluted solution were spread on agar plates. After an overnight incubation at 37° C. with/without 5% $CO_2$, CFU were enumerated. All these assays were performed at least in triplicates.

Determination of Bacterial Intracellular Boron and Magnesium Content by ICP-MS

The intracellular amount of boron in Neisseria sp. was determined (as done before [3]) by growing cells overnight on complete GCB and sub-culturing them in several agar plates containing 5 μM (1 μM for N. gonorrhoeae) of $NaBPh_4$ or $NaBF_4$. For this experiment, a no treatment control (bacteria grown on GCB alone) was also included. After incubating for 8 h, cells were suspended in PBS and centrifuged. Pellets were washed twice with PBS, respectively subjected to a 1 h digestion in nitric acid at 80° C. (500 μL, 65% solution, Sigma-Aldrich) followed by 16 h incubation at room temperature. The resulting solutions were diluted with water (HPLC grade, Fisher) to a final concentration of 3% in nitric acid. Samples were analyzed by inductively coupled plasma mass spectrometry (ICP-MS) with a Perkin Elmer NexION 300x (Perkin, USA) at the Department of Chemistry, Université de Montréal (Montréal, Canada). Results were expressed as the calculated ratio of boron (μg)/magnesium (μg). Experiments were carried out in triplicates.

Mice Infection

The strain LNP 24198 of Neisseria meningitidis expressing the luxCDABE gene under the control of the porBp promoter was used. Three groups, with five seven-week-old Balb/c mice each, were infected with luminescent Neisseria meningitidis. For this, 200 μL of bacterial cultures at $OD_{600nm}$ of 0.1 ($5×10^7$ cells/mL) mixed with 150 μL of human transferrin (20 mg/mL) was injected in each mouse. Two hours later, one group was treated with 100 μL of $NaBPh_4$ (20 μM) injected into the tail veins by intravenous injection (IV), and one group was treated with the same dose injected by intraperitoneal injection (IP). The remaining five were treated with 100 μL of DMSO as controls. $NaBPh_4$ was initially prepared at 20 mM in DMSO before being diluted into PBS to reach a final concentration of 20 μM (with 0.1% DMSO). DMSO was diluted in PBS in the same manner to achieve 1:1000. To test a possible toxicity of $NaBPh_4$, one group of 5 non-infected mice was treated with 100 μL of DMSO (IP) and two groups with 100 μL NaBPh4 (IV or IP). Luminescence was then measured, on the front and back of the mice, at different time points (0, 4, 8, 24 and 48 hours post-infection). The light signal was determined for each mouse using the ROI (Region Of Interest) tool of the IVIS Lumina III.

Compound Synthesis and Characterization

General Comments

All chemicals including sodium tetrakis(tolyl)borate (15), sodium tetrakis(4-fluorophenyl)borate (16), sodium tetraphenylborate (1), and sodium tetrafluoroborate (4) were purchased from commercial sources and used without further purification.

Figure 5:
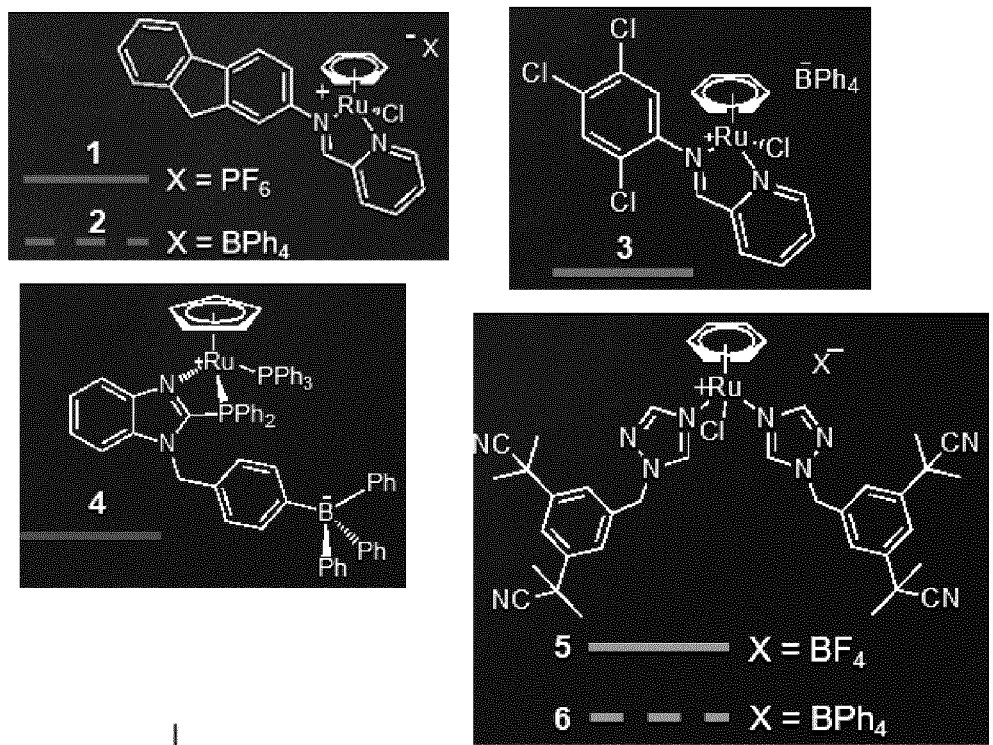
FIG. 5 is a graph showing the effect of $BPh_4$-functionalized Ru zwitterion (21) and various Ru+ ions with $BPh_4^-$, $BF_4^-$ or $PF_6^-$ counterions on the growth of *N. meningitidis* (16 h).
Figure 5:
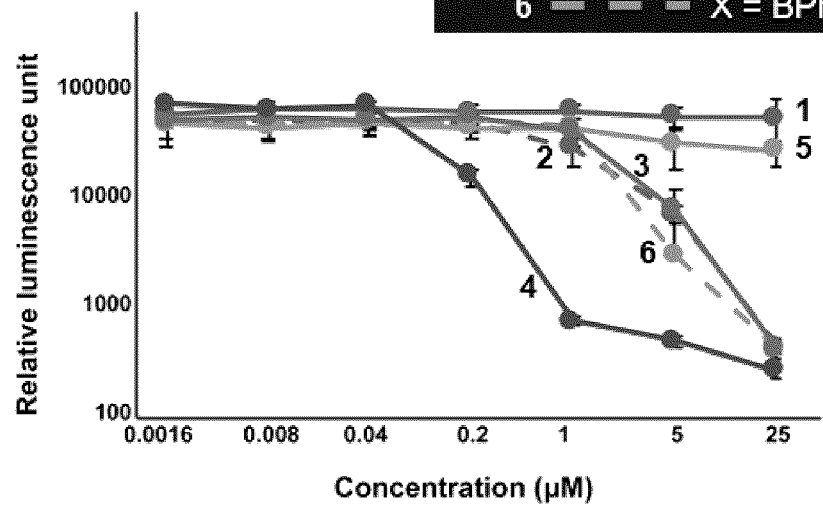

Potassium trifluoro(phenyl)borate (2), the zwitterion ruthenium complex (21), its corresponding ligand (20) and the cationic ruthenium complexes shown in FIG. 5 were prepared according to literature procedures by Mohy El Dine, T.; Sadek, O.; Gras, E.; Perrin, D. M. Expanding the Balz-Schiemann Reaction: Organotrifluoroborates Serve as Competent Sources of Fluoride Ion for Fluoro-Dediazoniation. Chem.—A Eur. J. 2018, 24 (56), 14933-14937; Golbaghi, G.; Haghdoost, M. M.; Yancu, D.; López De Los Santos, Y.; Doucet, N.; Patten, S. A.; Sanderson, J. T.; Castonguay, A. Organoruthenium(II) Complexes Bearing an Aromatase Inhibitor: Synthesis, Characterization, in Vitro Biological Activity and in Vivo Toxicity in Zebrafish Embryos. Organometallics 2019, 38 (3), 702-711; Haghdoost, M. M.; Golbaghi, G.; Guard, J.; Sielanczyk, S.; Patten, S. A.; Castonguay, A. Of the Counteranion †. 2019; and Walker, J. M.; Tassone, J. P.; Jenkins, H. A.; Spivak, G. J. The Synthesis of an Anionic, Tetraphenylborate-Functionalized, [P,N]-Hybrid Phosphinobenzimidazole Ligand and Its Hemilabile Behaviour in Ruthenium Zwitterion Chemistry. J. Organomet. Chem. 2014, 761, 56-63, all of which are incorporated herein by reference.

Reactions were performed under an inert atmosphere of nitrogen using Schlenk techniques and solvents were dried using a solvent purification system (Pure Process Technology).

NMR spectra ($^1H$, $13C\{1H\}$, COSY, HSQC, and HMBC) were recorded using a 600 MHz Bruker Avance III NMR spectrometer (QCI cryoprobe, 3 mm NMR tubes, 25° C.). Chemical shifts (δ) and coupling constants are expressed in ppm and Hz, respectively. $^1H$ and $^{13}C\{^1H\}$ spectra were referenced to solvent resonances, and spectral assignments were confirmed by 2D experiments. It is noteworthy that due to coupling, the signals corresponding to carbons that are directly linked to boron could sometimes not be observed in the $^{13}C\{^1H\}$ spectra.

High-resolution and high accuracy mass spectra (HR-ESI-MS) were obtained using an Exactive Orbitrap spectrometer from ThermoFisher Scientific (Department of Chemistry, McGill University).

Mass spectra (ESI-MS) were obtained using a Waters quarto premier mass spectrometer and used in direct injection mode.

HPLC-UV were obtained using an Agilent 1260 infinity II equipped with a pursuit C18 150×3.0 mm 3.0 μm column using a Milli-Q water and acetonitrile gradient.

A Perkin Elmer Nexion 300X ICP mass spectrometer was used for the determination of sodium and lithium levels (Department of Chemistry, Université de Montréal).

Partition coefficients (Log P) were determined using the shaking flask method (HPLC-UV)—see Román, I. P.; Mastromichali, A.; Tyrovola, K.; Canals, A.; Psillakis, E. Rapid Determination of Octanol-Water Partition Coefficient Using Vortex-Assisted Liquid-Liquid Microextraction. J. Chromatogr. A 2014, 1330, 1-5; and Yiantzi, E.; Psillakis, E.; Tyrovola, K.; Kalogerakis, N. Vortex-Assisted Liquid-Liquid Microextraction of Octylphenol, Nonylphenol and Bisphenol-A. Talanta 2010, 80 (5), 2057-2062, both of which are incorporated herein by reference.

General Procedure for the Synthesis of Grignard Reagents

Magnesium turnings (0.053 g, 2.18 mmol) were heated at 120° C. under reduced pressure for 1 h. THF (20 mL) was added followed by the addition of a small crystal of diiodine and the corresponding n-bromoalkane or bromoaryl (1.93 mmol). The mixture was brought to boil for 1-3 h, cooled to room temperature and used immediately.

General Procedure for the Synthesis of Triphenylalkylborates and Tolyltriphenylborate The corresponding Grignard reagent (0.60 mmol) was added dropwise (over 5 min) to a pre-cooled (−78° C.) solution of triphenyl boron (2 mL of a 0.25 M solution in THF) in THF (5 mL). The reaction mixture was kept at −78° C. for 2 h and was then allowed to slowly return to room temperature overnight. 10 mL of an aqueous sodium carbonate (0.5 M) solution were then added. The mixture was extracted with ethyl acetate and the solvent was evaporated under vacuum. The resulting oil was dissolved in dichloromethane, hexanes was added and the precipitate was filtered. Sodium methyltriphenylborate (5) was obtained as a white powder (0.070 g, 54%). $^1$H NMR (600 MHz, methanol-$d_4$) δ: 0.26 (q, J=3.89 Hz, 3H), 6.80 (tt, J=7.2, 1.5 Hz, 3H), 6.96 (t, J=7.5 Hz, 6H), 7.22-7.30 (m, 6H); $^{13}$C{$^1$H} NMR (151 MHz, methanol-$d_4$) δ: 13.42 (q, J=42.3 Hz), 122.40, 126.50, 135.53, 168.84 (q, J=48.2 Hz). ESI-MS m/z (−): 257.2 [M]$^-$ (Calc 257.2). Log P=−0.96±0.1. Sodium ethyltriphenylborate (6) was obtained as a white powder (0.070 g, 32%). $^1$H NMR (600 MHz, methanol-$d_4$) δ: 0.61-0.67 (m, 3H), 0.87-0.95 (m, 2H), 6.78 (tt, J=7.2, 1.5 Hz, 3H), 6.94 (t, J=7.3 Hz, 6H), 7.29-7.36 (m, 6H); $^{13}$C{$^1$H} NMR (151 MHz, methanol-$d_4$) δ: 12.40, 122.21, 126.34, 136.07, 167.59 (q, J=46.8 Hz). ESI-MS m/z (−): 271.2 [M]$^-$ (Calc 271.2). Log P=0.0±0.2. Sodium n-propyltriphenylborate (7) was obtained as a white powder (0.200 g, 47%). $^1$H NMR (600 MHz, DMSO-$d_6$) δ: 0.77-0.89 (m, 5H), 0.93 (p, J=7.1 Hz, 2H), 6.75 (tt, J=7.0, 1.5 Hz, 3H), 6.90 (t, J=7.4 Hz, 6H), 7.16-7.28 (m, 6H); $^{13}$C{$^1$H} NMR (151 MHz, DMSO-$d_6$) δ 165.77 (q, J=47.8 Hz), 134.37, 125.27, 121.08, 31.51 (q, J=39.6 Hz), 20.80, 19.79. ESI-MS m/z (−): 285.2 [M]$^-$ (Calc 285.2). Log P=0.8±0.2. Sodium tolyltriphenylborate (12) was obtained as a white powder (0.120 g, 77%). $^1$H NMR (600 MHz, methanol-$d_4$) δ: 2.22 (s, 3H), 6.79-6.85 (m, 5H), 6.97 (t, J=7.4 Hz, 6H), 7.16-7.22 (m, 2H), 7.26-7.33 (m, 6H); $^{13}$C{$^1$H}NMR (151 MHz, methanol-$d_4$) δ: 19.89, 121.24, 124.93, 125.79, 129.80, 135.88, 160.16 (q, J=49.8 Hz), 164.14 (q, J=48.5 Hz). ESI-MS m/z (−): 333.2 [M]$^-$ (Calc 333.2). Log P=0.41±0.02. Sodium butyltriphenylborate (8) was obtained as a white powder (0.120 g, 50%). $^1$H NMR (600 MHz, methanol-$d_4$) δ: 0.81 (t, J=7.4 Hz, 3H), 0.89-0.95 (m, 2H), 0.97-1.04 (m, 2H), 1.24 (h, J=7.3 Hz, 2H), 6.79 (t, J=7.4 Hz, 3H), 6.95 (t, J=7.4 Hz, 6H), 7.30-7.39 (m, 6H). $^{13}$C{$^1$H}NMR (151 MHz, methanol-$d_4$) δ: 13.62, 27.66 (q, J=42.3), 27.75, 30.46, 120.83, 124.98, 134.66, 166.55 (q, J=48.1 Hz). HR-ESI-MS m/z (−): 299.1980 [M]$^-$ (Calc 299.1977; Δ1.25 ppm) HR-ESI-MS m/z (+): 345.1770 [M+2Na]$^+$ (Calc 345.1761; Δ2.49 ppm) Log(P)=0.92±0.021. Sodium hexyltriphenylborate (9) was obtained as a white powder (0.213 g, 48%). $^1$H NMR (600 MHz, methanol-$d_4$) δ: 0.85 (t, J=6.7 Hz, 3H), 0.87-0.93 (m, 3H), 0.98-1.04 (m, 2H), 1.16-1.27 (m, 6H), 6.78 (tt, J=7.1, 1.4 Hz, 3H), 6.95 (t, J=7.5 Hz, 6H), 7.31-7.36 (m, 6H); $^{13}$C{$^1$H} NMR (151 MHz, methanol-$d_4$) δ: 14.67, 24.09, 29.19, 33.59, 36.17, 122.18, 126.33, 136.03, 167.93 (q, J=48.2 Hz, 2, 3, 5). ESI-MS m/z (−): 327.2 [M]$^-$ (Calc 327.2). Log P=2.83±0.02. Sodium heptyltriphenylborate (10) was obtained as a white powder (0.218 g, 47%). $^1$H NMR (600 MHz, methanol-$d_4$) δ: 0.86 (t, J=7.2 Hz, 3H), 0.88-0.93 (m, 2H), 0.98-1.04 (m, 2H), 1.15-1.25 (m, 6H), 1.27 (hept, J=7.1 Hz, 2H), 6.78 (tt, J=7.1, 1.5 Hz), 6.94 (t, J=7.5 Hz, 6H), 7.30-7.36 (m, 6H); $^{13}$C{$^1$H} NMR (151 MHz, methanol-$d_4$) δ: 13.19, 22.54, 27.82, 29.51, 32.14, 35.04, 120.81, 124.97, 134.67, 166.56 (q, J=47.0 Hz). ESI-MS m/z (−): 342.2 [M]$^-$ (Calc 342.2). Log P=3.10±0.05. Sodium octyltriphenylborate (11) was obtained as a white powder (0.255 g, 44%). $^1$H NMR (600 MHz, methanol-$d_4$) δ: 0.88-0.96 (m, 1H), 0.99-1.07 (m, 2H), 1.21-1.29 (m, 2H), 1.29-1.36 (m, 8H), 6.81 (t, J=7.2 Hz, 3), 6.97 (t, J=7.3 Hz, 6H), 7.32-7.40 (m, 6H). $^{13}$C{$^1$H}NMR (151 MHz, methanol-$d_4$) δ: 166.55 (q, J=47.7 Hz), 134.74, 125.11, 120.94, 35.09, 31.95, 29.83, 29.51, 27.81, 22.48, 13.21. ESI-MS m/z (−): 355.2 [M]$^-$ (Calc 355.3). Log P=4.1±0.3.

Synthesis of sodium (4-cyanophenyl)triphenylborate (17). p-bromobenzonitrile (0.444 g, 2.44 mmol) in anhydrous THF (20 mL) was cooled to −84° C. (ethyl acetate/liquid $N_2$). n-BuLi (1.52 mL of a 1.6 M solution, 2.44 mmol) was added dropwise to the cooled solution over about 5 min. The red solution was stirred for 40 min at −84° C. and BPh$_3$ was added (9.6 mL of a 0.25 M solution in THF) dropwise over 5 min. The solution was kept at −84° C. for 2 h and was then allowed to slowly return to room temperature overnight. 60 mL of hexanes were added, and the solution was placed in an ultrasound bath for 30 sec. The solution was decanted (5 times) over 30 min and the supernatant was removed. The resulting white precipitate was dried under vacuum (0.700 g, 58%). $^1$H NMR (600 MHz, acetone-$d_6$) δ: 6.82 (tt, J=7.2, 1.4 Hz, 4H), 6.96 (t, J=7.7 Hz, 6H), 7.25-7.30 (m, 8H), 7.48-7.52 (m, 2H). HR-ESI-MS m/z (+): 390, 1399 [M+2Na]$^+$ (Calc 390.1400; Δ1.78 ppm).

Synthesis of sodium (4-iodophenyl)triphenylborate (18). p-iodobenzene (0.18 g, 0.55 mmol) in anhydrous THF (20 mL) was cooled to −40° C. (ethanol/dry ice). iPrMgCl·LiCl (0.44 mL of a 1.3 M solution in THF, 0.57 mmol) was added dropwise to the cooled solution over about 5 min. The solution was stirred for two hours at −40° C. and BPh$_3$ was added (2 mL of a 0.25 M solution in THF) dropwise over 5 min. The solution was kept at −40° C. for 2 h and allowed to slowly return to room temperature overnight. The resulting oil was dissolved in dichloromethane. Hexanes was added and the resulting precipitate was filtered. The white precipitate was dried under vacuum (0.095 g, 41%). $^1$H NMR (600 MHz, methanol-$d_4$) δ: 6.86 (tt, J=7.2, 1.5 Hz, 3H), 6.99 (t, J=7.4 Hz, 6H), 7.06-7.09 (m, 2H), 7.25-7.29 (m, 8H); $^{13}$C{$^1$H} NMR (151 MHz, methanol-$d_4$) δ: 86.63, 121.44, 125.04, 133.77, 135.75, 138.51, 164.58 (q, J=49.6 Hz). ESI-MS m/z (−): 445.0 [M]$^-$ (Calc 445.1).

Synthesis of sodium tris(4-methylphenyl)(phenyl)borate (14). To a suspension of potassium trifluoro(phenyl)borate (0.200 g, 1.09 mmol) in anhydrous THF (20 mL) was added and three equivalent of a solution of corresponding Grignard reagents was added dropwise over 5 minutes. The solution was stirred overnight at room temperature. After completion 10 ml of 0.5 M sodium carbonate was added and extract with ethyl acetate and dry under vacuum. The resulting oil was dissolved in dichloromethane and hexane was added, the resulting precipitate was filtered. The final product was obtained as a white powder (0.107 g, 25%). $^1$H NMR (600 MHz, acetone-$d_6$) δ: 2.17 (s, 9H), 6.72-6.79 (m, 7H), 6.91 (t, J=7.3 Hz, 2H), 7.21-7.26 (m, 6H), 7.32-7.37 (m, 2H); $^{13}$C{$^1$H} NMR (151 MHz, acetone-$d_6$) δ: 20.44, 121.14, 124.98, 125.92, 129.16, 136.17, 160.75 (q, J=49.3 Hz), 164.79 (q, J=49.0 Hz). Log(P)=2.5±0.2. ESI-MS m/z (−): 360.2 [M]$^-$ (Calc 360.2).

Synthesis of Heterocyclic compound (22). The synthesis was adapted from the procedure reported in ang, M.; Nudelman, F.; Matthes, R. R.; Shaver, M. P. Frustrated Lewis Pair Polymers as Responsive Self-Healing Gels. *J. Am. Chem. Soc.* 2017, 139 (40), 14232-14236, incorporated herein by reference. Triisopropyl borate (10.63 mmol; 2 g) in anhydrous THF (40 ml) was cooled to −78° C. and two equivalent of phenyl magnesium bromide at 3M (21.27 mmol) was added dropwise over 15 minutes. The solution was kept at −78° C. for 2 h and allowed to slowly return to room temperature overnight. After completion, 10 mL of 1 M HCl aqueous solution was added and extract with ethyl acetate and dry under vacuum. The resulting oil was dissolved in ethyl acetate and an excess of ethanolamine was added, and stirred overnight. The solution was washed with distilled water and dried with $MgSO_4$. The solution was dried under vacuum and the precipitate recrystallized with a mixture of dichloromethane/hexanes. The final product was obtained as a white powder (1.260 g, 55%).

Synthesis of potassium difluorodiphenylborate (3). The synthesis was adapted from the procedure reported in Ito, T.; Iwai, T.; Mizuno, T.; Ishino, Y. Palladium-Catalyzed Cross-Coupling Reaction of Potassium Diaryldifluoroborates with Aryl Halides. Synlett 2003, No. 10, 1435-1438, incorporated herein by reference. To a solution of 2-aminoethyldiphenyl borate (0.200 g, 0.89 mmol) in 5 mL of methanol were added 3 equivalents of potassium bifluoride and the reaction mixture was stirred for 1 h. The excess of potassium bifluoride was filtered and the solvent evaporated under vacuum. The resulting powder was stirred for a few hours in diethyl ether and then filtered. The final product was obtained as a white powder (0.200 g, 93%).

Synthesis of sodium bis(4-methylphenyl)diphenylborate (13). To a solution of potassium difluorodiphenylborate (0.250 g, 1.03 mmol) in anhydrous THF (20 mL) cooled to −78° C. was added and 2.5 equivalent of a solution of tolylmagnesium bromide at 0.5 M (0.74 mmol) was added dropwise over 5 minutes. The solution was stirred overnight at room temperature. After completion 10 mL of 0.5 M sodium carbonate was added and extract with ethyl acetate and dry under vacuum. The resulting oil was dissolved in dichloromethane and hexanes was added, the resulting precipitate was filtered the final product was obtained as a white powder (0.120 g, 59%). $^1H$ NMR (600 MHz, DMSO-$d_6$) δ: 2.15 (s, 6H), 6.73 (d, J=7.4 Hz, 4H), 6.76 (t, J=7.3 Hz, 2H), 6.90 (t, J=7.3 Hz, 4H), 7.00-7.07 (m, 4H), 7.12-7.20 (m, 4H); $^{13}C\{^1H\}$ NMR (151 MHz, DMSO-$d_6$) δ: 21.30, 121.84, 125.67, 126.58, 129.77, 135.97, 160.23 (q, J=49.0 Hz), 164.27 (q, J=50.2 Hz). ESI-MS m/z (−): 347.4 [M]$^-$ (Calc 347.2), 717.7 [2M+Na]$^-$ (Calc 717.4). Log(P)=2.0±0.1.

Synthesis of sodium {4-[(E)-[(2-hydroxynaphthalen-1-yl)methylidene]amino]phenyl}triphenylborate (19). 2-hydroxy-1-napthaldehyde (0.850 g, 4.49 mmol) in ethanol (15 mL) was added parabromobenzylamine (0.851 g, 4.49 mmol) and bring to reflux for 6 h. The middle was place at minus 18 overnight. The yellow precipitate was filter and wash with methanol. Yellow crystalline 1-[(1E)-[(4-bromophenyl)imino]methyl]naphthalen-2-ol was obtained (1.300 g, 81%) after the residue was dried under reduced pressure. $^1H$ NMR (600 MHz, chloroform-$d_3$) δ: 7.12 (d, J=9.4 Hz, 1H), 7.24 (d, J=9.0 Hz, 2H), 7.36 (t, J=7.9 Hz, 1H), 7.54 (d, J=8.4 Hz, 1H), 7.57 (d, J=9.0 Hz, 2H), 7.72-7.75 (m, 1H), 7.83 (d, J=9.4 Hz, 1H), 8.11 (d, J=9.1 Hz, 1H), 9.35 (d, J=4.0 Hz, 1H), 15.24 (d, J=3.2 Hz, 1H). $^{13}C\{^1H\}$NMR (151 MHz, chloroform-$d_3$) δ: 168.49, 155.80, 145.22, 136.61, 133.03, 132.69, 129.43, 128.16, 127.50, 123.72, 122.13, 121.51, 119.88, 118.98, 109.03. ESI-MS m/z (+): 328 [M+H]$^+$; 653 [2M+H]$^+$. 1-[(1E)-[(4-bromophenyl)imino]methyl]naphthalen-2-ol (0.214 g, 0.66 mmol) in THF (40 mL) was cooled to −94° C. (acetone/liquid $N_2$). nBuLi (0.82 mL of a 1.6 M solution, 1.312 mmol) was added dropwise to the cooled solution over about 5 min and turned to a transparent red solution. A solution of $BPh_3$ (2.6 mL of a 0.25 M solution in THF) was added immediately after dropwise over 5 min. The solution was kept at −94° C. for 2 h and slowly returned to room temperature overnight. 10 mL of methanol was added and the middle evaporate under vacuum. The compound was purified on normal phase 100% ethyl acetate to 25 MeOH/75 ethyl acetate (v/v) and the polar fraction was purified on reversed phase 40% water-methanol to 100% methanol (v/v). The collected fraction was dried under vacuum to give an orange powder (0.080 g, 25%). The nature of counterion was determined by ICP-MS: 63.7% sodium and 37.3% lithium. HR-ESI-MS m/z (−): found 488.2173 [M]$^-$ (Calc 488.2191; Δ2.66 ppm); HR-ESI-MS m/z (+): 983.4515 [2M+Li]$^+$ (Calc 983.4537; Δ1.78 ppm). Elemental analysis calculated (%) for: $C_{35}H_{27}BNONa_{0.63}Li_{0.37}$+2 $H_2O$: C, 77.61, H, 5.77, N, 2.59, found (%): C, 77.17, H, 5.75, N, 2.59. $^1H$ NMR (600 MHz, methanol-$d_4$) δ: 6.78 (d, J=9.3 Hz, 1H), 6.88 (t, J=7.2 Hz), 7.02 (t, J=7.4 Hz, 6H), 7.13 (d, J=8.4 Hz, 2H), 7.20 (t, J=7.4 Hz, 1H), 7.33 (t, J=6.1 Hz, 6H), 7.42 (t, J=7.7 Hz, 1H), 7.45-7.50 (m, 2H), 7.54 (d, J=7.9 Hz, 1H), 7.67 (d, J=9.3 Hz, 1H), 8.06 (d, J=8.4 Hz, 1H), 9.24 (s, 1H); $^{13}C\{^1H\}$ NMR (151 MHz, methanol-$d_4$) δ: 180.15, 164.62 (q, J=49.0 Hz), 150.87, 139.57, 138.62, 137.17, 135.54, 135.05, 130.18, 129.45, 127.55, 126.49, 125.95, 123.99, 122.88, 119.82, 116.94, 108.37, 49.43.

Example 2: Library Screening for the Identification of Compounds with the Ability to Inhibit the Growth of *N. meningitidis*

To screen molecules for their antibacterial activity, a luminescent system was used, as previously described for other bacteria [1]. A clinical isolate of *N. meninigitidis* (LNP24198) expressing luciferase (LuxABCDE) under the control of the constitutive promoter porBp was used, as similarly described [2], located in the intergenic region next to NMB1732. More than 2400 compounds from different origins were screened to identify candidates with the ability to inhibit the growth of *N. meningitidis* after 16 h at 37° C. As presented in FIG. 1A, showing a sample of these results, only 17 compounds (around 0.7% of the library) were able to completely inhibit the growth of *N. meningitidis* at 100 μM. For these experiments, erythromycin was used as a positive control (FIG. 1B) (<800 RLU, the background light, was found to be the largest value measured with 10 replicates of erythromycin 3.5 μM, known to inhibit all possible growth of *N. meningitidis*). It is noteworthy that stock solutions for all tested compounds were prepared in DMSO and that the final DMSO concentration of the tested solutions was kept at 1%, a concentration which has proven not to affect the growth of *N. meningitidis* (FIG. 1A). Interestingly, it was noted that four (4) of the active compounds identified harbored a $BPh_4^-$ (tetraphenylborate anion) (FIG. 1C) and were found to be the only molecules from the screened library to include this moiety (AnIII-7, AnIII-6, AnII-18, $NaBPh_4$, see structure in FIG. 1D). An investigation of the effect of the $BPh_4^-$ moiety was then pursued.

Example 3: $BPh_4^-$ Efficiently Kills *N. meningitidis* and *N. gonorrhoeae*

The library screen allowed the identification of candidates with significant bacteriostatic activity, but did not provide information about their bactericidal effect. Therefore, the bactericidal activity was assessed for the 4 compounds harboring a $BPh_4^-$ identified from the initial screen described above (AnIII-7, AnIII-6, AnII-18, $NaBPh_4$). *N. meningitidis* was treated with 50 µM of each compound and the % survival cells (compared with DMSO 1% control) was measured using serial dilutions and CFU counts. After 3 h, the detection of any live bacteria was not possible, as seen in FIG. 2A. To verify if the bactericidal effect could be observed for the other pathogen of the *Neisseria* family, a clinical isolate of. *N. gonorrhoeae* (LNP16626 [3]) was also treated with 50 µM of the same compounds, respectively, using the same assay. Again, no viable cells were detected after 3 h, suggesting that $BPh_4^-$ is also toxic for *N. gonorrhoeae*. It may thus be concluded that $BPh_4^-$ exhibits bactericidal activity against pathogenic *Neisseria* species such as *N. meningitidis* and *N. gonorrhoeae* and that $BPh_4^-$ could potentially be exploited as a bactericidal agent or to increase the bactericidal effect of other compounds.

Example 4: $BF_4^-$ a Tetrahedral Boron Ion Analogue, does not Efficiently Kill *N. meningitidis* and *N. gonorrhoeae*

To determine whether the effect of $BPh_4^-$ on the two pathogens of the *Neisseria* family was specific to this ion or shared by other tetrahedral boron ions, the two bacteria were respectively exposed to 50 µM of two analogues of AnIII-7 and AnIII-6 (notably AnIII-8 and AnIII-17, see structure in FIG. 2C) for which the only structural difference is the nature of their counterion ($BF_4^-$ instead of $BPh_4^-$). Under these conditions, the two analogues did not display a similar effect than their $BPh_4^-$ counterparts, providing evidence that the bactericidal activity of $BPh_4^-$ is not shared by all tetrahedral boron ions.

Example 5: Several $BPh_4^-$ Salts ($Na^+$, $K^+$ and $NH_4^+$) are Toxic to *N. meningitidis*

To exclude any salt-specific effect, the effect of several $BPh_4^-$ and $BF_4^-$ salts on the growth of *N. meningitidis* luminescent strain was tested. The growth of *N. meningitidis* was measured after a 16 h-exposure to different concentrations of various $BPh_4^-$ and $BF_4^-$ salts. These results are presented in FIG. 3. From this assay, the MIC (minimum inhibitory concentration, the lowest concentration that prevents visible bacterial growth, <800 RLU) was calculated. All $BPh_4$ salts tested (sodium, ammonium and potassium) were all highly toxic for *N. meningitidis*. As observed for analogous $BPh_4^-/BF_4^-$ complexes previously tested, $BPh_4^-$ salts were found to be more active than their $BF_4^-$ counterparts (sodium and ammonium). No observable toxicity was noticed when the pathogen was exposed to neutral triphenylborane, $BPh_3$. These results show that $BPh_4^-$ (but not $BF_4^-$ nor $BPh_3$) is toxic to *Neisseria meningitidis* regardless of its nature.

Figure 4A:
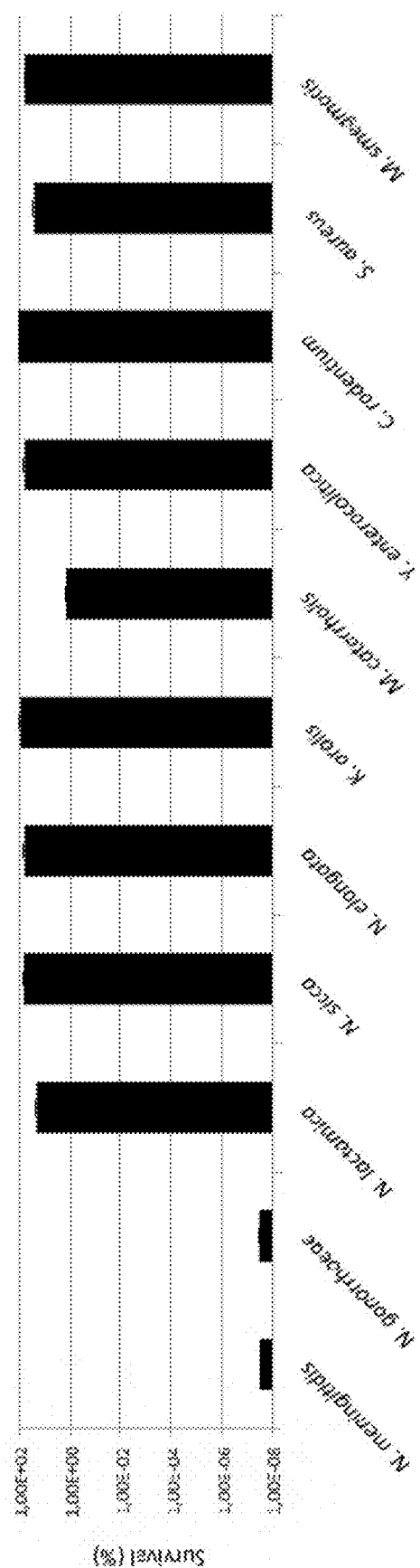
FIG. 4A shows the percentage of survival of a panel of strains exposed at a 50 µM concentration of $NaBPh_4$. Each bar represents the average of three independent measurements.
Figure 4B:
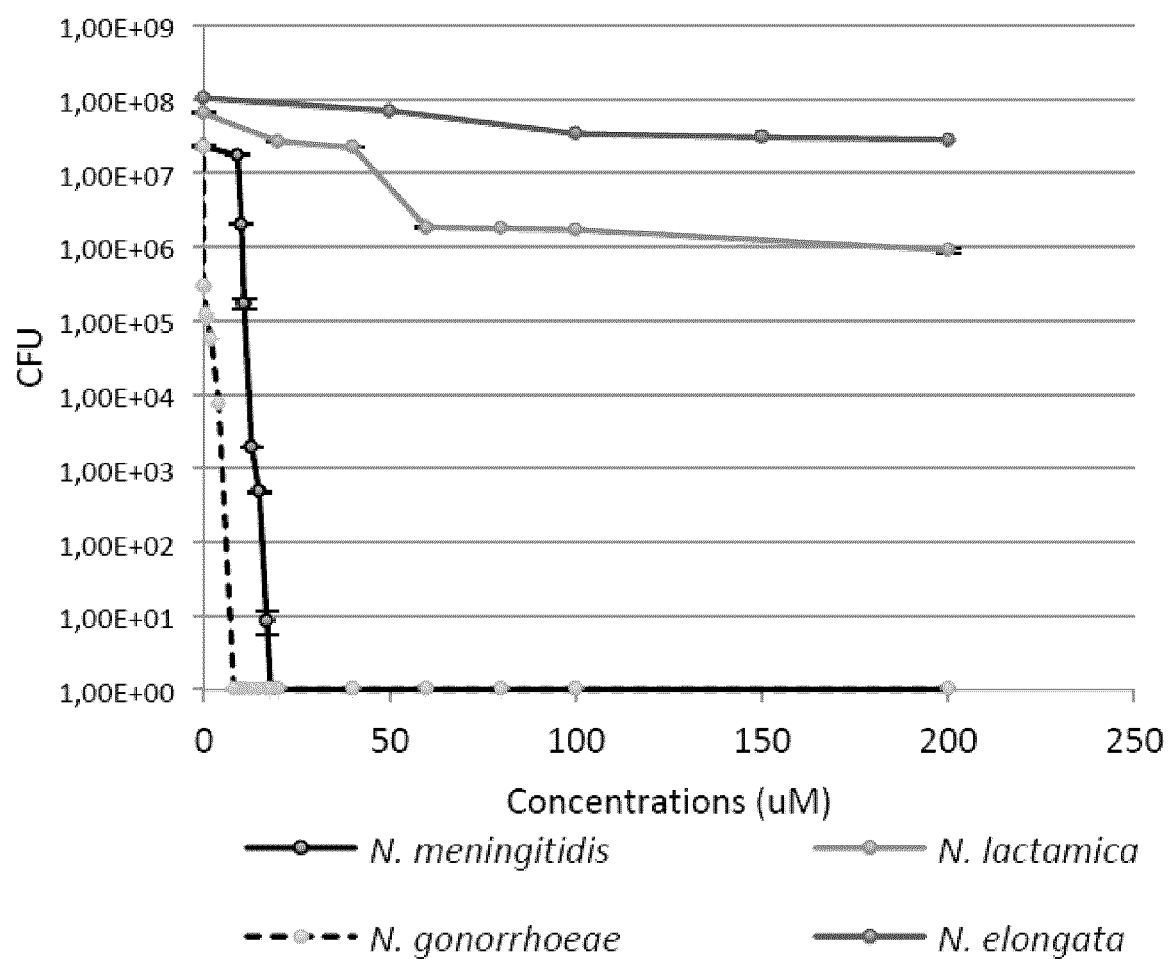
FIG. 4B shows the concentration-dependent survival (expressed in %) for 4 selected strains. Each point represents the average of three independent measurements.

Example 6: Only *N. meningitidis* and *N. gonorrhoeae* are Completely Cleared after a 3 h Exposure to $NaBPh_4$ To verify if the toxicity of $BPh_4^-$ is specific to the *Neisseria* genus, the percentage of survival of several *Neisseria* species was assessed after treatment with 50 µM of $NaBPh_4^-$ for 3 h (FIG. 4A). The results show that closely related *Neisseria* species *N. lactamica* were not as sensitive to $NaBPh_4^-$ treatment as the two pathogenic species *N. meningitidis* and *N. gonorrhoeae*. This result could not be expected considering their close phylogenetic proximity [4]. Other strains of *Neisseria* such as *N. sicca* and *N. elongate* were also tested, and they were also found to be less sensitive to $NaBPh_4$. Similar results were obtained with *Kingella oralis*, which is part of the Neisseriaceae family. These results provide evidence that the effect of $BPh_4^-$ is selective the two pathogenic species *N. meningitidis* and *N. gonorrhoeae*. Other Gram-negative species such as *Yersinia enterocolitica* and *Citrobacter rodentium* (order Enterobacterales) or *Moraxella catarrhalis* (order Pseudomonadeles), but also Gram-positive species such as *Staphylococcus aureus* and Actinobacteria with *M. smegmatis*, were also tested. Again, all of them were significantly more resistant to $NaBPh_4^-$ than *N. meningitidis* and *N. gonorrhoeae*.

The MBC (minimum bactericidal concentration that kill >99.999%), the concentration necessary to completely abrogate bacterial survival after a 3 h exposure to $NaBPh_4$, was next assessed. CFU counts for four species tested, *N. elongata, N. lactamica, N. meningitidis* and *N. gonorrhoeae* are presented in FIG. 4B. *N. gonorrhoeae* and *N. meningitidis* (that is capsulated) were clearly found to be the most sensitive species to $NaBPh_4^-$ with a respective MBC of 7.5 µM and 18 µM, whereas *N. lactamica* and *N. elongata* were found to have a lower sensitivity to this salt, with a MBC higher than 200 µM.

Figure 4C:
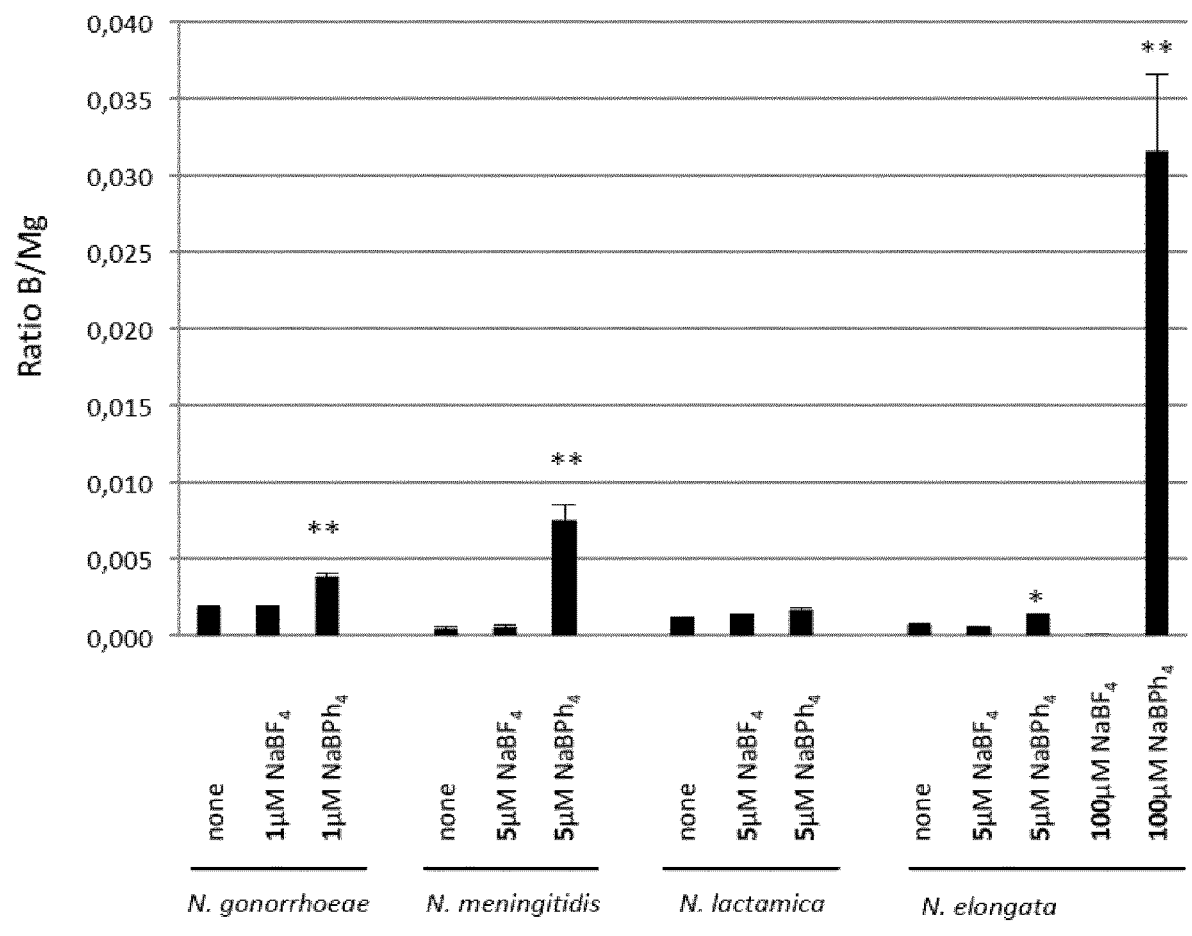
FIG. 4C shows the ICP-MS quantification of atoms contents (Mg, B), for strains of *N. gonorrhoeae, N. meningitidis, N. lactamica* and *N. elongata* and grown in rich medium with or without $NaBPh_4$ or $NaBF_4$. The data are expressed in ratio B/Mg. Each bar represents the average of three independent measurements (**$p<0.001$).

Example 7: Intracellular Boron Levels are Higher in *N. meningitidis* and *N. gonorrhoeae* than in Other *Neisseria* Species after Growth in Agar Media Containing $NaBPh_4$ In order to elucidate the specific effect of $BPh_4^-$ on the two pathogenic species *N. meningitidis* and *N. gonorrhoeae*, boron cellular uptake was assessed by inductively coupled plasma mass spectrometry (ICP-MS) after a 6 h of growth in agar media containing $NaBPh_4^-$ of four strains (*N. elongata, N. lactamica, N. meningitidis* and *N. gonorrhoeae*), as previously described [3] (FIG. 4C). Due to the higher sensitivity of *N. gonorrhoeae* to $BPh_4^-$, a lower concentration of $NaBPh_4^-$ was used for boron uptake experiments involving this strain. In comparison to a no treatment control (growth on GCB agar), a >2-fold increase in boron intracellular levels was noted when *N. gonorrhoeae* was exposed to 1 µM of $NaBPh_4$. It is interesting to note that when the same strain was exposed to 1 µM $NaBF_4$, the boron uptake was found to be similar to the control. When *N. meningitidis* was exposed to 5 µM of $NaBPh_4$, a 7-fold increase in intracellular boron levels was observed relative to the control (growth on GCB agar or with the same concentration of $NaBF_4$), whereas the boron uptake was found to be less than 2-fold (relative to respective controls) for other *Neisseria* species tested at the same concentration. This suggests that the internalization of boron (and putatively $BPh_4^-$) is superior for the two pathogenic species relative to the other *Neisseria* species tested.

Example 8: Increased Intracellular Boron Levels are Observed when *N. elongata* is Exposed to a High Concentration of $NaBPh_4$, as Compared to when Exposed to the Same Concentration of $NaBF_4$ To get more insights about the difference in the ability of $BPh_4^-$ and $BF_4^-$ to internalize bacteria of the *Neisseria* family, *N. elongata* was exposed to 100 µM of $NaBPh_4$ and $NaBF_4$, respectively (FIG. 4C). When treated with this high concentration, boron levels were found to be 61-fold higher in the case of NaBPh$_4$, relative to NaBF$_4$. It can then be concluded that boron internalizes more readily in this strain when in the form of BPh$_4^-$, relative to BF$_4^-$. These results also suggest that BPh$_4^-$ toxicity remains low for this non-pathogenic bacterium, even when allowed to massively internalize. It is noteworthy that these experiments could not be performed with *N. meningitidis* (due to its high sensitivity to BPh$_4^-$ at this concentration).

Example 9: Activity of Borate Compounds on *N. meningitidis*

Several borate compounds were prepared and their ability to inhibit *N. meningitidis* growth was assessed using the luminescent system described at Example 2. The minimum inhibitory concentration of the tested compounds is reported in Table I below.

TABLE 1

| Compound | MIC (μM) |
|---|---|
| 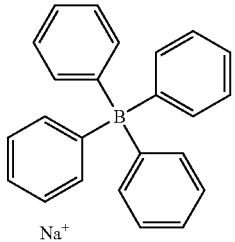<br>Sodium tetraphenylborate (1) | 15 |
| 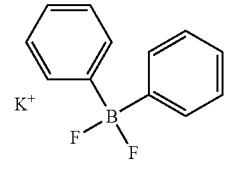<br>Potassium difluorodiphenylborate (3)<br>Comparative | 37.5 |
| 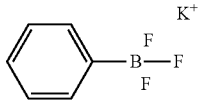<br>Potassium trifluoro(phenyl)borate (2)<br>Comparative | >250 |
| 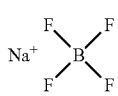<br>Sodium tetrafluoroborate (4) | >250 |

TABLE 1-continued

| Compound | MIC (μM) |
|---|---|
| 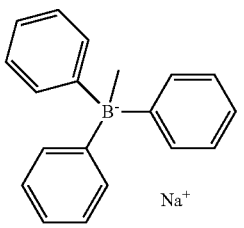<br>Sodium methyltriphenylborate (5) | 25 |
| 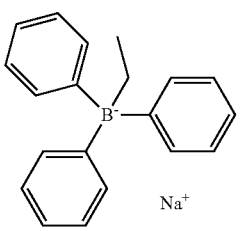<br>Sodium ethyltriphenylborate (6) | 25 |
| 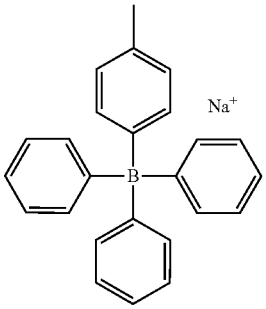<br>Sodium tolyltriphenylborate (12) | 25 |
| 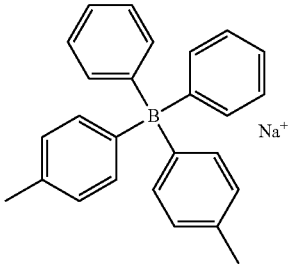<br>Sodium bis(4-methylphenyl)diphenylborate (13) | 5 |
| 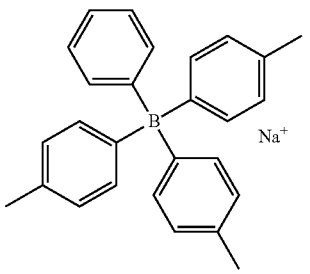<br>Sodium tris(4-methylphenyl)(phenyl)borate (14) | 5 |

TABLE 1-continued

| Compound | MIC (μM) |
|---|---|
| 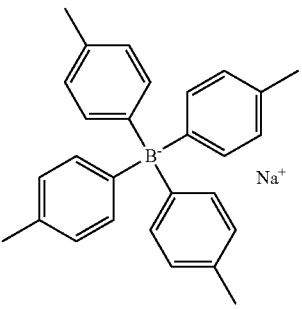
Sodium tetrakis(tolyl)borate (15) | Active but MIC not determined because of abnormal background signal |
| 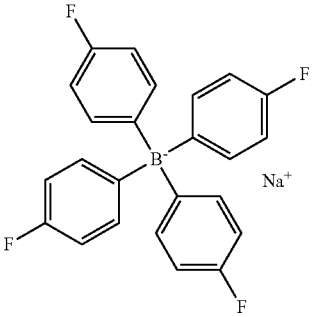
Sodium tetrakis(4-fluorophenyl)borate (16) | 2.5 |
| 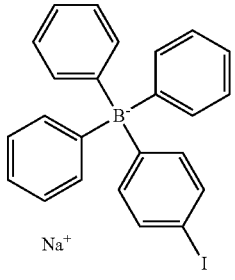
Sodium (4-iodophenyl)triphenylborate (18) | 2.35 |
| 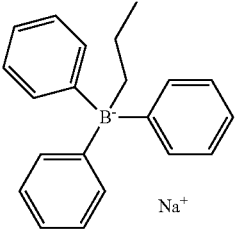
Sodium n-propyltriphenylborate (7) | 5 |
| 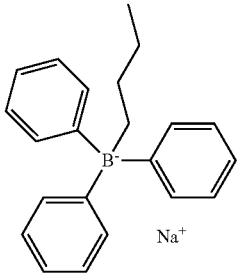
Sodium butyltriphenylborate (8) | 5 |
| 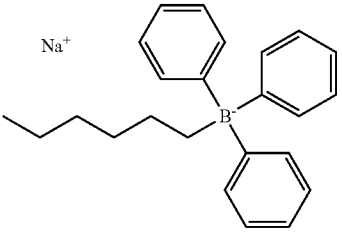
Sodium hexyltriphenylborate (9) | 1 |
| 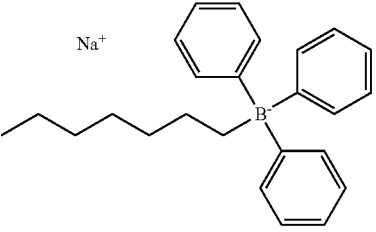
Sodium heptyltriphenylborate (10) | 1 |
| 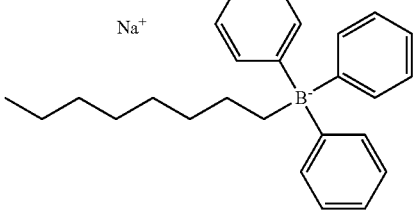
Sodium octyltriphenylborate (11) | 1 |
| 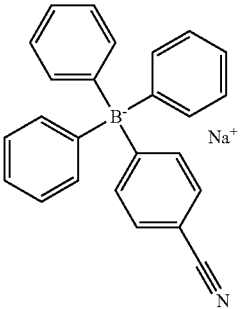
Sodium (4-cyanophenyl)triphenylborane (17) | Active (MIC similar to NaBPh$_4$) |

TABLE 1-continued

| Compound | MIC (µM) |
|---|---|
| Sodium {4-[(E)-[(2-hydroxynaphthalen-1-yl)methylidene]amino]phenyl}triphenylborate (19) | 2.35 |
| Zwitterion ruthenium complex (21) | 0.78 |
| Corresponding ligand (20) | 0.78 |
| Heterocyclic compound (22) | 75 |

The results depicted in FIG. 5 show that the activity of the above BPh$_4$-functionalized Ru zwitterion (21). It also shows that various Ru+ ions with a BPh4$^-$ counterion, all of which were synthesized according the methods reported in the literature, but not with a BF$_4$— or PFs counterion, have the ability to inhibit the growth of *N. meningitidis*. Note that compound 6 in FIG. 5 corresponds to AnII-18 in FIG. 2C.

Figure 6:
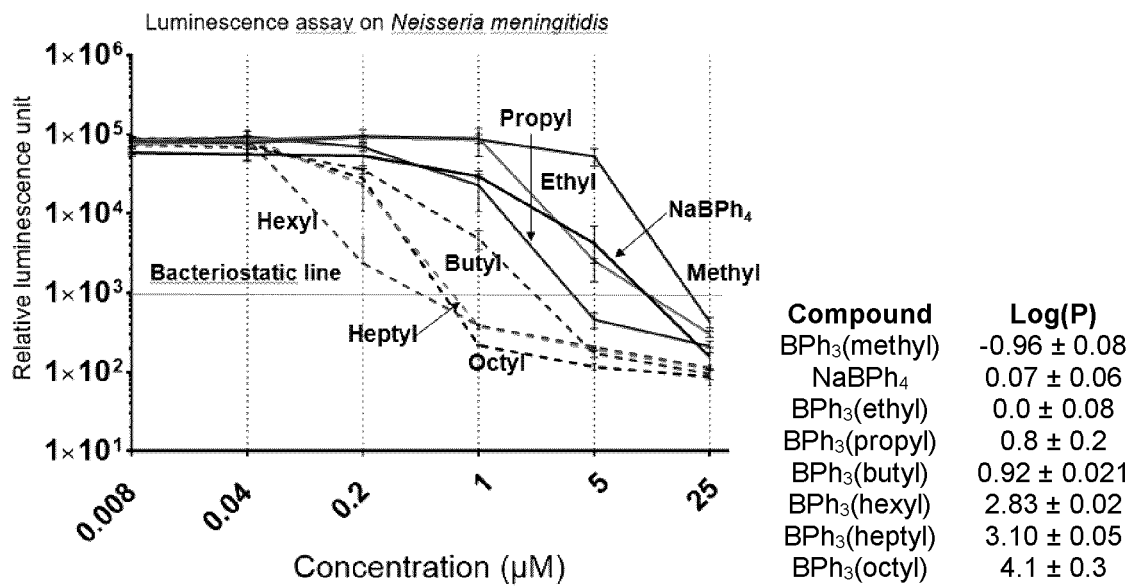
FIG. 6 is a graph showing the effect of several alkyltriphenylborate compounds having different lipophilicity on the growth of *N. meningitidis* (16 h).

The results depicted in FIG. 6 show that the lipophilicity of the alkyltriphenylborate compounds influences the antibacterial activity against *N. meningitidis*, with more lipophilic compounds typically showing higher potency. In line with this observation, BF$_4$, which does not exhibit antibacterial activity against *N. meningitidis* and *N. gonorrhoeae* (see Example 4), has a Log P of about −1.6 (hydrophilic).

Figure 7A:
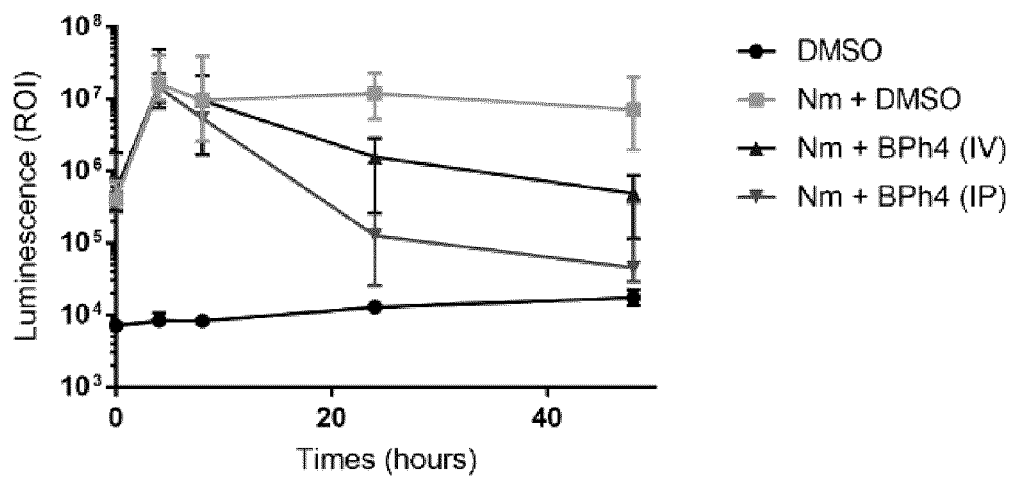
FIG. 7A is a graph showing the quantification of the bacterial load at different time point post-infection in mice infected with a luminescent strain of *N. meningitidis*.
Figure 7B:
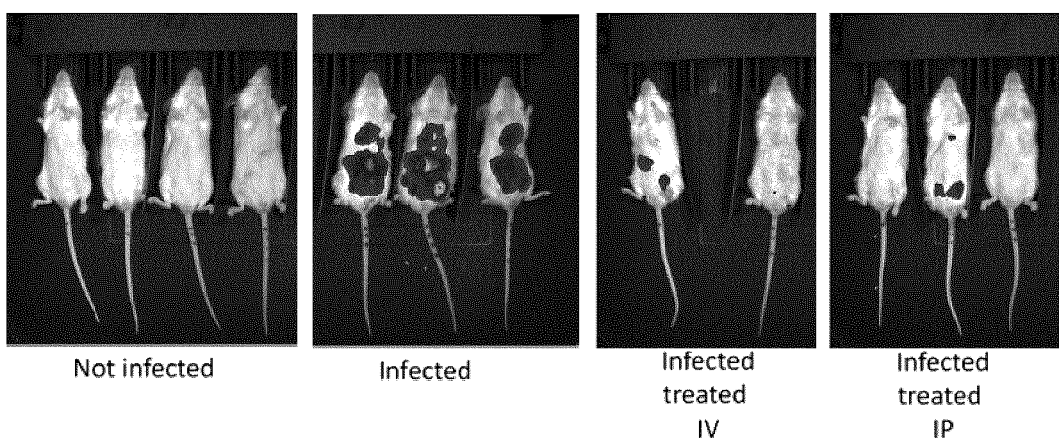
FIG. 7B are images of mice 24 h after infection with a luminescent strain of *N. meningitidis*.

Example 10: Administration of NaBPh$_4^-$ Treats *N. meningitidis* Infection In Vivo The effect of NaBPh$_4$ administration in a murine model of *N. meningitidis* infection was assessed. The results presented in FIGS. 7A and 7B show that intravenous (IV) or intraperitoneal (IP) administration of NaBPh$_4$ significantly reduces the *N. meningitidis* bacterial load at 24 h and 48 h post-infection, relative to infected mice administered with the vehicle only (DMSO). No apparent sign of toxicity was observed in mice treated with NaBPh$_4$.

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Shawar R M, Humble D J, Van Dalfsen J M, Stover C K, Hickey M J, Steele S, et al. Rapid screening of natural products for antimycobacterial activity by using luciferase-expressing strains of *Mycobacterium bovis* BCG and *Mycobacterium intracellulare*. Antimicrob Agents Chemother. 1997; 41(3):570-4. PubMed PMID: 9055994; PubMed Central PMCID: PMCPMC163752.
2. Guiddir T, Deghmane A E, Giorgini D, Taha M K. Lipocalin 2 in cerebrospinal fluid as a marker of acute bacterial meningitis. BMC Infect Dis. 2014; 14:276. doi: 10.1186/1471-2334-14-276. PubMed PMID: 24885531; PubMed Central PMCID: PMCPMC4033677.
3. Veyrier F J, Boneca I G, Cellier M F, Taha M K. A novel metal transporter mediating manganese export (MntX) regulates the Mn to Fe intracellular ratio and *Neisseria meningitidis* virulence. PLoS Pathog. 2011; 7 (9): e1002261. Epub 2011/10/08. doi: 10.1371/journal.ppat.1002261. PubMed PMID: 21980287; PubMed Central PMCID: PMC3182930.
4. Bennett J S, Bentley S D, Vernikos G S, Quail M A, Cherevach I, White B, et al. Independent evolution of the core and accessory gene sets in the genus *Neisseria*: insights gained from the genome of *Neisseria lactamica* isolate 020-06. BMC Genomics. 2010; 11:652. doi: 10.1186/1471-2164-11-652. PubMed PMID: 21092259; PubMed Central PMCID: PMCPMC3091772.

Mohy El Dine, T.; Sadek, O.; Gras, E.; Perrin, D. M. Expanding the Balz-Schiemann Reaction: Organotrifluoroborates Serve as Competent Sources of Fluoride Ion for Fluoro-Dediazoniation. Chem.—A Eur. J. 2018, 24 (56), 14933-14937. https://doi.org/i0.1002/chem.201803575.

Golbaghi, G.; Haghdoost, M. M.; Yancu, D.; López De Los Santos, Y.; Doucet, N.; Patten, S. A.; Sanderson, J. T.; Castonguay, A. Organoruthenium(II) Complexes Bearing an Aromatase Inhibitor: Synthesis, Characterization, in Vitro Biological Activity and in Vivo Toxicity in Zebrafish Embryos. Organometallics 2019, 38 (3), 702-711. https://doi.org/10.1021/acs.organomet.8b00897.

Haghdoost, M. M.; Golbaghi, G.; Guard, J.; Sielanczyk, S.; Patten, S. A.; Castonguay, A. Of the Counteranion t. 2019. https://doi.org/10.1039/c9dt00143c.

Walker, J. M.; Tassone, J. P.; Jenkins, H. A.; Spivak, G. J. The Synthesis of an Anionic, Tetraphenylborate-Functionalized, [P,N]-Hybrid Phosphinobenzimidazole Ligand and Its Hemilabile Behaviour in Ruthenium Zwitterion Chemistry. J. Organomet. Chem. 2014, 761, 56-63. https://doi.org/10.1016/j.jorganchem.2014.03.003.

Román, I. P.; Mastromichali, A.; Tyrovola, K.; Canals, A.; Psillakis, E. Rapid Determination of Octanol-Water Partition Coefficient Using Vortex-Assisted Liquid-Liquid Microextraction. J. Chromatogr. A 2014, 1330, 1-5. https://doi.org/10.1016/j.chroma.2014.01.003.

Yiantzi, E.; Psillakis, E.; Tyrovola, K.; Kalogerakis, N. Vortex-Assisted Liquid-Liquid Microextraction of Octylphenol, Nonylphenol and Bisphenol-A. Talanta 2010, 80 (5), 2057-2062. https://doi.org/10.1016/j.talanta.2009.11.005.

Wang, M.; Nudelman, F.; Matthes, R. R.; Shaver, M. P. Frustrated Lewis Pair Polymers as Responsive Self-Healing Gels. J. Am. Chem. Soc. 2017, 139 (40), 14232-14236. https://doi.org/10.1021/jacs.7b07725.

Ito, T.; Iwai, T.; Mizuno, T.; Ishino, Y. Palladium-Catalyzed Cross-Coupling Reaction of Potassium Diaryldifluoroborates with Aryl Halides. Synlett 2003, No. 10, 1435-1438. https://doi.org/i0.1055/s-2003-40851.

What is claimed is:

1. A method for treating a pathogenic *Neisseria* infection in a subject comprising administering an effective amount of a borate compound to said subject, wherein the borate compound is of formula (I):

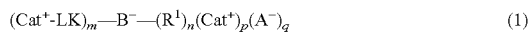

$$(Cat^+-LK)_m—B^-—(R^1)_n(Cat^+)_p(A^-)_q \quad (1)$$

wherein:
  m and n are integers from 0 to 4, with the proviso that m+n=4,
  p is an integer and is the larger of 0 and 1-m,
  q is an integer and is the larger of 0 and m−1,
  each $R^1$ independently represents:
    alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being unsubstituted or substituted with one or more of the following:—$R^2$, —$OR^2$, —$P(R^2)_2$, —$SR_2$, —O—CO—$R^2$, —CO—O—$R^2$, —CO—$R^2$, —CO—N($R^2)_2$, —N($R^2)_2$, —N$R_2$—CO—$R^2$, —C=N$R_2$, —C≡N, —$NO_2$, —$N_3$, halogen, or -LK-$R^3$,
  each $R^2$ independently represents:
    alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being unsubstituted or substituted with one or more of the following:— $R^4$, —$OR^4$, —$P(R^4)_2$, —$SR_4$, —O—CO—$R^4$, —CO—O—$R^4$, —CO—$R^4$, —CO—N($R^4)_2$, —N($R^4)_2$, —N$R_4$—CO—$R^4$, —C=N$R_4$, —C≡N, —$NO_2$, —$N_3$, halogen, or -LK-$R^3$, or —H, —OH, —$P(R^4)_2$, —SH, —O—CO—H, —COOH, —CO—H, —CO—NH2, —NH2, —NH—CO—H, —C=NH, —C≡N, —$NO_2$, —$N_3$, halogen, or -LK-$R^3$,
  each $R^3$ independently represents is a pharmaceutically acceptable metal-based complex;
  each $R^4$ independently represents: H, alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, heteroaryl, —OH, —SH, —O—CO—H, —COOH, —CO—H, —CO—NH2, —NH2, —NH—CO—H, —C=NH, —C≡N, —$NO_2$, —$N_3$, halogen, or -LK-$R^3$,
  each -LK- independently represents a covalent bond or one or more of the following, alone or in combination: amide, amine, imine, —C(=O)—, —S—, —S—S—, —O—, ester, alkylene, alkenylene, alkynylene, alkenylnylene, cycloalkylene, cycloalkenylene, cycloalkynylene, cycloalkenynylene, heterocycloalkylene, heterocycloalkenylene, heterocycloalkynylene, heterocycloalkenynylene, arylene, or heteroarylene,
  each $Cat^+$ independently represents a pharmaceutically acceptable cation which is:
    (i) an alkali metal cation;
    (ii) an alkaline earth metal cation;
    (iii) a metal cation;
    (iv) an inorganic amine cation;
    (iv) a cation of an organic base; or
    (v) a cationic metal-based complex, and
  each $A^-$ independently represents a pharmaceutically acceptable anion, which is aceglutamate, acephyllinate, acetamidobenzoate, acetate, acetylasparaginate, acetylaspartate, adipate, aminosalicylate, anhydromethylenecitrate, ascorbate, aspartate, benzoate, benzylate, besylate, bicarbonate, bisulphate, bitartrate, borate, bromide, butylbromide, camphorate, camsylate, carbonate, chloride, chlorophemoxyacetate, citrate, closylate, cromesilate, cyclamate, dehydrochloate, dihydrochloride, dimalonate, edetate, edisylate, estolate, esylate, ethylbromide, ethylsulfate, fendizoate, fluoride, formate, fosfatex, fumarate, gluceptate, gluconate, glucoronate, glutamate, glycerophosphate, glycinate, glycollylarsinilate, glycyrrhizate, hippurate, hemisulphate, hexylresorcinate, hybenzate, hydrobromide, hydrochloride, hydroiodide, hydroxybenzenesulfonate, hydroxybenzoate, iodide, isethionate, lactate, lactobionate, lysine, malate, maleate, mandalate, mesylate, methylbromide, methyliodide, methylnitrate, methylsulphate, monophosadenine, mucate, napadisylate, napsylate, nicotinate, nitrate, oleate, orotate, oxalate, oxoglurate, pamoate, pantothenate, pectinate, phenylethylbarbiturate, phosphate, picrate, policrilix, polistirex, pyridoxylphosphate, polygalacturonate, propionate, saccharinate, salicylate, stearate, stearylsulphate, subacetate, succinate, sulfate, sulfosalicylate, tannate, tartrate, teprosilate, terephthalate, teoclate, thiocyanate, timonaciate, tosylate, triethiodide, undecanoate, and xinafoate,
  with the proviso that no more than two $R^1$ are halogen and with the proviso that the borate compound comprises at least two $R^1$, which are aryl or heteroaryl, both of which being unsubstituted or substituted with one or more of the following:—$R^2$, —$OR^2$, —$P(R^2)_2$, —$SR_2$, —O—CO—R², —CO—O—R², —CO—R², —CO—N(R²)₂, —N (R²)₂, —NR₂—CO—R², —C=NR₂, —C≡N, —NO₂, —N₃, halogen, or -LK-R³.

2. The method of claim 1, wherein m is 0 or 1.
3. The method of claim 1, wherein no more than one R¹ is halogen.
4. The method of claim 1, wherein:
each R¹ is independently alkyl, alkenyl, alkynyl, alkenynyl, cycloalkyl, cycloalkenyl, cycloalkynyl, cycloalkenynyl, heterocycloalkyl, heterocycloalkenyl, heterocycloalkynyl, heterocycloalkenynyl, aryl, or heteroaryl, all of which being unsubstituted or substituted with one or more-R², —OR², —P(R²)₂, —SR₂, —O—CO—R², —CO—O—R², —CO—R², —CO—N(R²)₂, —N(R²)₂, —NR₂—CO—R², —C=NR₂, —C≡N, —NO₂, —N₃, halogen, or -LK-R³,
or
one or two R¹ are halogen and the remaining R¹ are aryl or heteroaryl.
5. The method of claim 1, wherein:
when R¹ is a group substituted with R², and R² is:
alkyl, alkenyl, alkynyl, alkenynyl, a halogen atom, or —C≡N,
aryl or heteroaryl,
and
in —N(R²)₂ groups, one R² is —H and the other R² is aryl or heteroaryl,
wherein the aryl and heteroaryl are unsubstituted or substituted with one or more of the following:—R⁴, —OR⁴, —P(R⁴)₂, —SR₄, —O—CO—R⁴, —CO—O—R⁴, —CO—R⁴, —CO—N(R⁴)₂, —N(R⁴)₂, —NR₄—CO—R⁴, —C=NR₄, —C≡N, —NO₂, —N₃, halogen, or -LK-R³.
6. The method of claim 1, wherein R⁴ is H, aryl or heteroaryl.
7. The method of claim 1, wherein-LK-represents a covalent bond or one or more of the following, alone or in combination, —O—, alkylene, alkenylene, alkynylene, alkenylnylene, or heteroarylene.
8. The method of claim 7, wherein:
-LK-represents alkylene combined with —O— to form one or more alkyleneoxy groups,
or
-LK-represents heteroarylene, alone or combined with one or more of the following groups on each side of the heteroarylene: alkylene, alkenylene, alkynylene, or alkenylnylene,
or
-LK-represents arylene alone or combined with one or more of the following groups: alkylene, alkenylene, alkynylene, or alkenylnylene groups.
9. The method of claim 1, wherein R³ represents

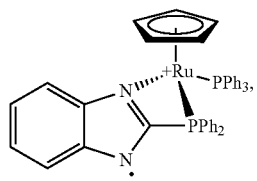

wherein the dot represents the point of attachment.
10. The method of claim 1, wherein R³ represents a ruthenium-based complex.

11. The method of claim 1, wherein the pharmaceutically acceptable cation is:

(i) Na⁺, Li⁺, or K⁺;

(ii) such as Ca²⁺ or Mg²⁺;

(iii) an aluminum cation, iron cation, zinc cation, copper cation, nickel cation, or cobalt cation;

(iv) ammonium (NH₄⁺) or an ethyl ammonium, diethylammonium, trimethylammonium tetraethylammonium, tetramethylammonium or tetrabutylammonium cation;

(v) a cation of chloroprocaine, dibenzylamine, dicyclohexylamine, a dicyclohexylamine, diethanolamine, ethylamine, ethylenediamine, glucosamine, guanidine, a methylamine, morpholine, choline, N,N'-dibenzylethylenediamine, N-benzyl-phenethylamine, N-methylglucamine, phenylglycine alkyl ester, piperazine, piperidine, procaine, t-butyl amines, tetramethylammonium, t-octylamine, tris-(2-hydroxyethyl)amine, or tris(hydroxymethyl)aminomethane cations; or (vi) a cationic ruthenium complex.

12. The method of claim 11, wherein the pharmaceutically acceptable cation is:
Na⁺, K⁺, NH₄⁺,

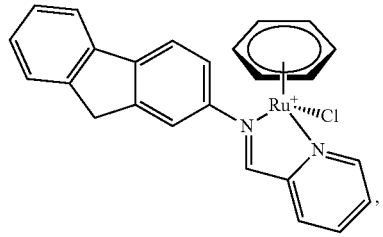

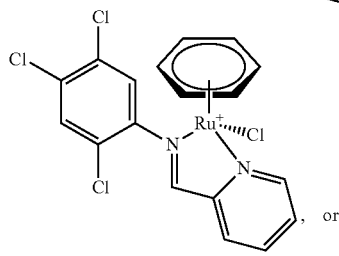
, or

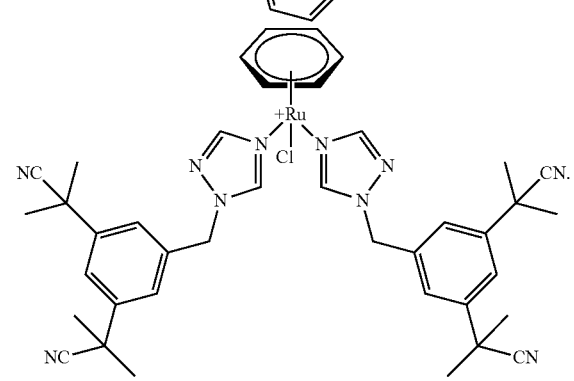

13. The method of claim 1, wherein the pharmaceutically acceptable anion is acetate, besylate, bisulphate, bromide, carbonate, chloride, citrate, fluoride, formate, iodide, maleate, mesylate, methylsulphate, nitrate, nitrite, pamoate, phosphate, stearate, sulfate, or tartrate.

14. The method of claim 1, wherein the borate compound is of formula:
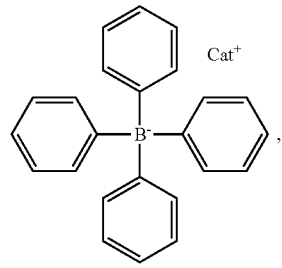
(IV)
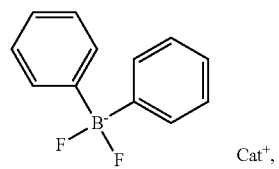
(V)
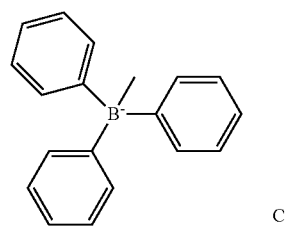
(VI)
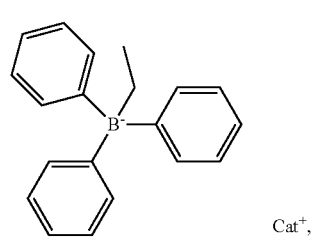
(VII)
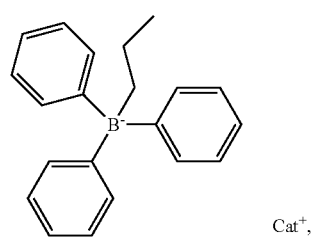
(VIII)
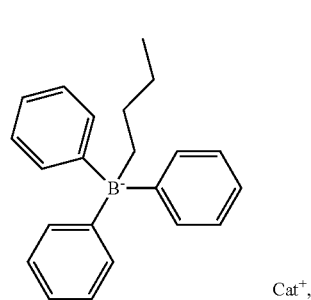
(IX)
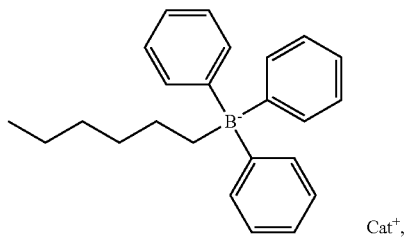
(X)
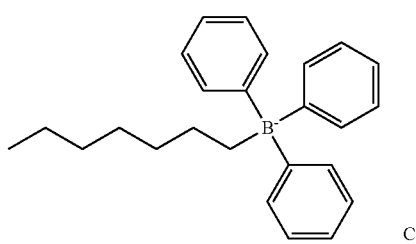
(XI)
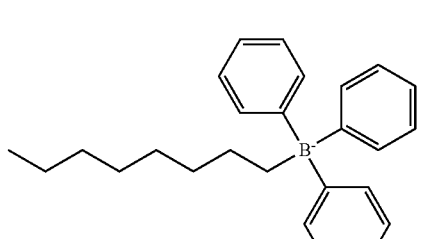
(XII)
-continued
(XIII)
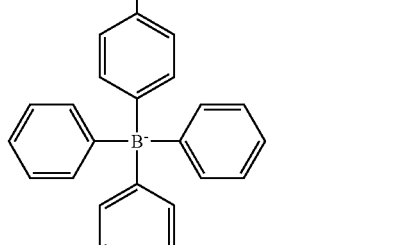
(XIV)
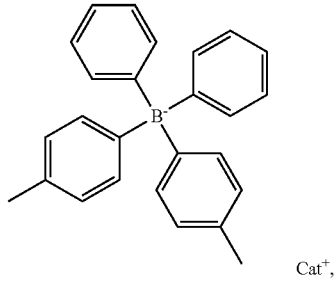

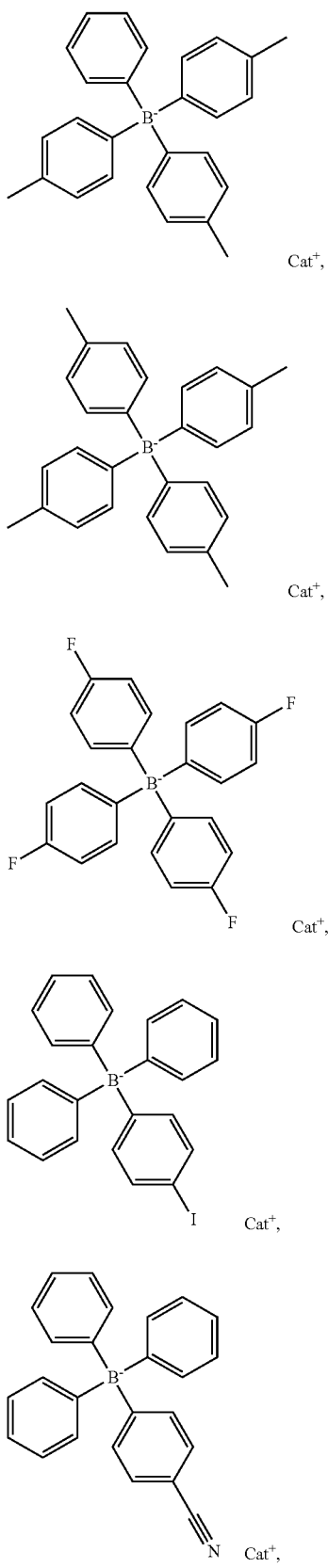

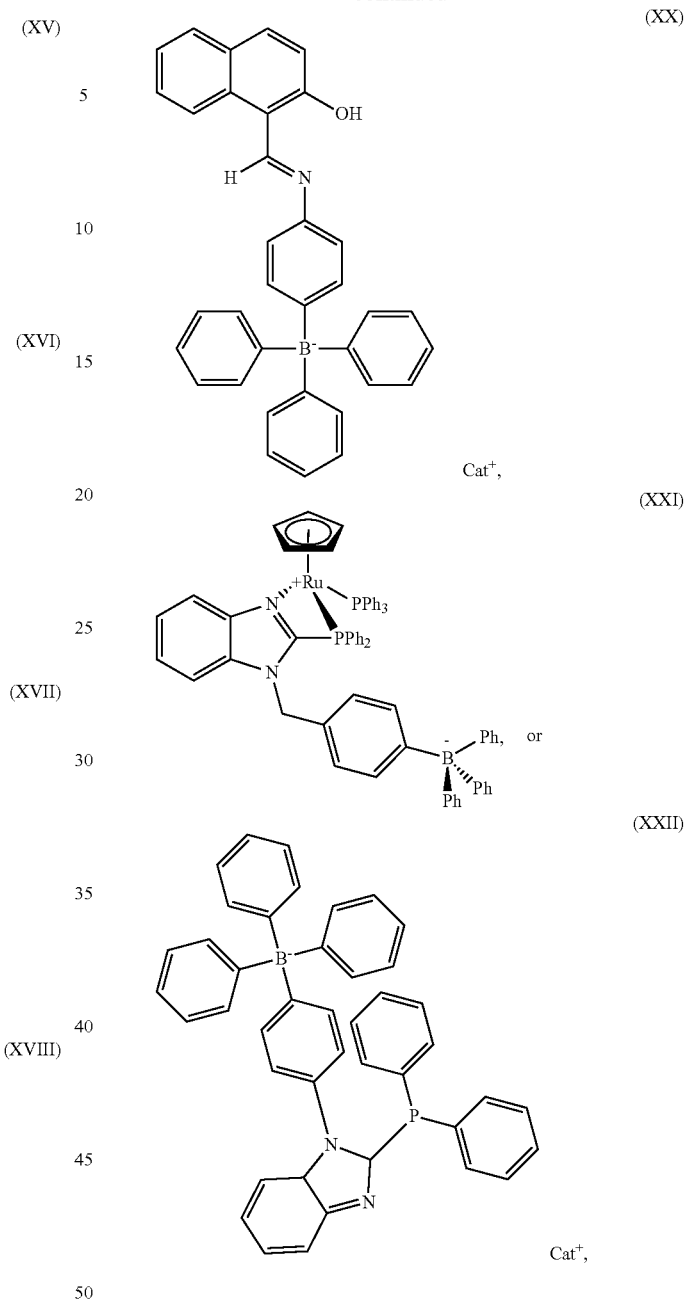

wherein Cat⁺ is as defined in claim 1.

15. A method for inhibiting the growth and/or killing pathogenic *Neisseria* bacteria, the method comprising contacting said pathogenic *Neisseria* bacteria with an effective amount of a borate compound as defined in claim 1.

16. The method of claim 1, wherein the pathogenic *Neisseria* bacteria is *Neisseria meningitidis* and/or *Neisseria gonorrhoeae*.

17. The method of claim 1, wherein the pathogenic *Neisseria* bacteria is resistant to one or more antibiotics.

18. The method of claim 1, wherein the borate compound is formulated into a pharmaceutical composition comprising at least one carrier or excipient.

19. The method of claim 1, wherein the borate compound is administered or used in combination with at least one additional antibiotic.

20. The method of claim 1, wherein the borate compound comprises at least two $R^1$, which are phenyl.

\* \* \* \* \*